(12) United States Patent
Green et al.

(10) Patent No.: US 11,246,979 B2
(45) Date of Patent: Feb. 15, 2022

(54) INSTRUMENTS AND METHODS FOR LOADING CELLS INTO IMPLANTABLE DEVICES

(71) Applicant: ViaCyte, Inc., San Diego, CA (US)

(72) Inventors: Chad Green, San Diego, CA (US); Laura Martinson, San Diego, CA (US); Erik Olson, San Diego, CA (US); Val Anthony Bellora, San Diego, CA (US); Leah Elliott, San Diego, CA (US); Richard Alexander Grant, San Diego, CA (US); Donald Koenig, San Diego, CA (US); Giacomo Strollo, San Diego, CA (US)

(73) Assignee: ViaCyte, Inc., San Diego, CA (US)

( * ) Notice: Subject to any disclaimer, the term of this patent is extended or adjusted under 35 U.S.C. 154(b) by 0 days.

(21) Appl. No.: 16/912,227

(22) Filed: Jun. 25, 2020

(65) Prior Publication Data
US 2020/0324043 A1    Oct. 15, 2020

Related U.S. Application Data

(62) Division of application No. 15/528,731, filed as application No. PCT/US2014/060306 on Nov. 20, 2014, now Pat. No. 10,722,644.

(51) Int. Cl.
*A61M 5/14* (2006.01)
*A61M 5/142* (2006.01)
(Continued)

(52) U.S. Cl.
CPC ......... *A61M 5/14276* (2013.01); *A61F 2/022* (2013.01); *A61M 5/142* (2013.01);
(Continued)

(58) Field of Classification Search
CPC .............. A61M 5/142; A61M 5/14276; A61M 37/0069; A61M 2209/045; B65B 3/003; C12N 5/0676
(Continued)

(56) References Cited

U.S. PATENT DOCUMENTS 4,242,459 A ‡ 12/1980 Chick ................... A61F 2/022
                                                    128/DIG. 3
5,011,472 A ‡ 4/1991 Aebischer ............ A61F 2/022
                                                    604/15
(Continued)

FOREIGN PATENT DOCUMENTS

EP    1174156 A2 ‡ 1/2002 ............. A61L 27/38
EP    1174156 A2    1/2002
(Continued)

OTHER PUBLICATIONS

European Examination Report dated Jul. 10, 2018, issued in connection with corresponding European Patent Application No. 14906271.3 (8 pages total).‡

(Continued)

*Primary Examiner* — Timothy L Maust
(74) *Attorney, Agent, or Firm* — Klarquist Sparkman, LLP

(57) ABSTRACT

Embodiments herein describe tools, instruments and methods for aseptic loading, dispensing and/or delivering cells into an implantable device and aseptically and selectively sealing a device inside a sterile package as well as and storing and preparing for shipment the cell-filled device.

17 Claims, 13 Drawing Sheets

(51) Int. Cl.
  *B65B 3/00* (2006.01)
  *A61F 2/02* (2006.01)
  *A61M 37/00* (2006.01)
  *C12N 5/071* (2010.01)

(52) U.S. Cl.
  CPC ......... *A61M 37/0069* (2013.01); *B65B 3/003* (2013.01); *A61M 2209/045* (2013.01); *C12N 5/0676* (2013.01)

(58) Field of Classification Search
  USPC ..................................................... 604/502
  See application file for complete search history.

(56) References Cited

U.S. PATENT DOCUMENTS

| | | | | |
|---|---|---|---|---|
| 5,158,881 A | ‡ | 10/1992 | Aebischer | A61F 2/022 435/18 |
| 5,555,920 A | * | 9/1996 | Godolphin | A61J 1/2089 141/130 |
| 5,837,444 A | ‡ | 11/1998 | Shah | A61K 9/0024 435/4 |
| 5,976,780 A | ‡ | 11/1999 | Shah | C12N 11/04 424/42 |
| 6,617,151 B1 | * | 9/2003 | Newman | A61F 2/022 424/424 |
| 7,418,981 B2 | * | 9/2008 | Baker | A61J 1/2089 141/104 |
| 9,033,911 B2 | * | 5/2015 | de Juan, Jr. | A61M 5/46 604/36 |
| 9,259,526 B2 | * | 2/2016 | Barron | G16H 40/00 |
| 9,433,557 B2 | * | 9/2016 | Green | A61F 2/022 |
| 9,883,987 B2 | ‡ | 2/2018 | Lopez | A61M 5/14228 |
| 10,722,644 B2 | * | 7/2020 | Green | A61M 5/14276 |
| 2009/0081296 A1 | ‡ | 3/2009 | Humes | A61M 1/3653 424/48 |
| 2011/0067781 A1 | ‡ | 3/2011 | Osborne | B65B 3/003 141/37 |
| 2014/0014226 A1 | ‡ | 1/2014 | Green | A61J 1/20 141/18 |
| 2015/0327875 A1 | * | 11/2015 | Look | A61B 17/32037 604/508 |

FOREIGN PATENT DOCUMENTS

| | | | |
|---|---|---|---|
| JP | H06-234164 | ‡ | 8/1994 |
| JP | 2008-023346 | ‡ | 2/2008 |
| JP | 2008023346 A | | 2/2008 |
| WO | 2015160348 A1 | | 10/2015 |
| WO | WO-2015/160348 A1 | ‡ | 10/2015 ............. A61B 50/30 |

OTHER PUBLICATIONS

European Search Report dated Jun. 28, 2018, issued in connection with corresponding European Patent Application No. 14906271.3 (4 pages total).‡

International Search Report and Written Opinion dated Aug. 20, 2015 issued in connection with PCT/US2014/060306 (14 pages total).‡

Japanese Office Action dated Oct. 15, 2018 issued in connection with corresponding Japanese Patent Application No. 2017-527636 (9 pages total).‡

\* cited by examiner
‡ imported from a related application

SEALING THE DEVICE:

WITH THE DFPA 62 STILL IN THE DEVICE CASE NESTING BLOCK 30, MULTI-POSITION BLOCK 58 AND SLIDING CARRIAGE 22, TURN ON THE HAND-HELD RF SEALER 68 AND PLACE THE C-SHAPED JAWS OF THE SEALER 68 AROUND THE DFPA 62 NEAR THE AREA OF THE DEVICE PORT 72.

USING THE HANDLE SQUEEZE THE ELECTRODES 70 TOGETHER ON EITHER SIDE OF THE DEVICE PORT 72 AND APPLY SUFFICIENT PRESSURE ON THE ELECTRODES 70 TO SEAL THE DEVICE PORT 72.

RELEASE THE ELECTRODES 70 AND DEVICE PORT 72 SHOULD BE SEALED WHILE THE DFPA 62 SHOULD NOT BE SEAKED TO THE DEVICE PORT 72 OR TO ITSELF 62 OR THE ELECTRODES 70.

MOVE THE SLIDING CARRIAGE 22 TO THE FULLY-DISENGAGED POSITION AND REMOVE THE DFPA 62 WITH THE LOADED AND SEALED DEVICE 200.

— 322

SEALING THE DEVICE CASE STORAGE BAG:

PLACE A STERILE DEVICE CASE STORAGE BAG 124 IN BETWEEN THE FIRST PLATES 88 AND SWINGING PLATES OF THE DEVICE CASE STORAGE BAG HOLDER 76 OF THE SEALING STATION 2 AND SECURE BY RELEASING OR REPOSITIONING THE CLAMP LEVER 112.

CAREFULLY OPEN THE DFPA 62, THEN USING STERILE SCISSORS CUT OFF ANY EXCESS SEALED LOADING PORT 72 AND REMOVE THE DEVICE CASE 74 WITH THE SEALED DEVICE 200 AND PLACE IT IN THE STERILE UNSEALED DEVICE CASE STORAGE BAG 124 IN BETWEEN THE FIRST HOLDER PLATES 88.

FILL THE BAG 124 WITH THE APPROPRIATE STRORAGE MEDIUM TO SUBMERGE AND BATHE THE DEVICE CASE 74 AND SEALED DEVICE 200.

CLOSE THE SWINGING PLATES 90 USING THE CAM LEVER 98 TO EXPEL ANY RESIDUAL AIR IN THE BAG 124.

MOVE THE SLIDING CARRIAGE 106 UNDER THE SEALING HEAD ASSEMBLY 78.

CLAMP THE ELECTRODES 84, 86 AROUND THE UNSEALED DEVICE CASE STORAGE BAG 124 BY EXTENDING THE AIR CYLINDER 81, THEN TURN ON THE SEALING ELECTRODES 84, 86 MOMENTARILY AND SEAL THE BAG 124 WITH THE DEVICE CASE 74 AND THE CELL-FILLED AND SEALED DEVICE 200 IN THE STORAGE MEDIUM INSIDE THE SEALED BAG 124.

— 324

SEALING THE SHIPPING BAG:

PLACE AN UNSEALED STERILE SHIPPING BAG 126 IN THE SHIPPING BAG HOLDER 118.

PLACE THE SEALED DEVICE CASE STORAGE BAG 124 INTO THE OPEN, UNSEALED SHIPPING BAG 126.

TURN ON THE SHIPPING BAG SEALER 120 AND PLACE THE OPEN UNSEALED PORTION OF THE SHIPPING BAG 126 UNDER THE SEALING BAR 122. ACTUATE THE SEALING BAR 122 TO LOWER IT, APPLY PRESSURE AND HEAT AND SEAL THE SHIPPING BAG 126.

INSTRUMENTS AND METHODS FOR LOADING CELLS INTO IMPLANTABLE DEVICES

CROSS-REFERENCE TO RELATED APPLICATIONS

The present application is a divisional of U.S. patent application Ser. No. 15/528,731, filed May 22, 2017, which is the U.S. National Stage of International Application No. PCT/US2014/060306, filed Nov. 20, 2014, both of which applications are incorporated herein by reference.

STATEMENT OF GOVERNMENT SUPPORT

This research was made possible, in part, by an award from the California Institute for Regenerative Medicine (Award No. DR1-01423). The contents of this publication are solely the responsibility of the inventors and do not necessarily represent the official views of CIRM or any other agency of the state of California.

BACKGROUND OF THE INVENTION

1. Field of Invention

The present invention relates generally to a cellular therapy and means and methods for loading and filling an implantable device with cells and sealing the device with the cells therein.

2. Description of Related Art

Cell replacement therapy for certain diseases can be therapeutically treated by transferring cells, tissues, or organs into a patient having the particular disease. The main hurdles to a commercial cell therapy remain a renewable cell source and an encapsulation source which provides allo-protection against host immunity. Ideally, such an implantable device provides allo-protection and minimizes or eliminates patient use of long term immune-suppressive drugs.

Previously, Applicants have described both a renewable cell source and macro-encapsulation drug delivery system suitable for at least the purpose of pancreatic progenitor cell delivery for production of insulin in vivo in response to glucose stimulation. See, for example, at least U.S. application Ser. No. 12/099,759, entitled METHODS OF PRODUCING PANCREATIC HORMONES, filed Apr. 8, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. No. 14/106,330, entitled IN VITRO DIFFERENTIATION OF PLURIPOTENT STEM CELLS TO PANCREATIC ENDODERM CELLS (PEC) AND IMMATURE BETA CELLS, filed Dec. 12, 2013; Ser. No. 14/201,630, filed Mar. 7, 2014; and PCT/US2014/026529, IN VITRO DIFFERENTIATION OF PLURIPOTENT STEM CELLS TO PANCREATIC ENDODERM CELLS (PEC) AND ENDOCRINE CELLS, filed Mar. 13, 2014; PCT/US2014/022109, 3-DIMENSIONAL LARGE CAPACITY CELL ENCAPSULATION DEVICE, filed Mar. 7, 2014; U.S. Design application Nos. 29/408,366 filed Dec. 12, 2011; 29/408,368 filed Dec. 12, 2011; 29/423,365 filed May 31, 2012; 29/447,944 filed Mar. 13, 2013; 29/484,363, 29/484,359, 29/484,360, 29/484,357; 29/484,356, 29/484,355, 29/484,362 and 29/484,35, titled 3-DIMENSIONAL LARGE CAPACITY CELL ENCAPSULATION DEVICE and filed Mar. 7, 2014; PCT/US2014/034425, TOOLS AND INSTRUMENTS FOR USE WITH IMPLANTABLE ENCAPSULATION DEVICES, filed Apr. 16, 2014; U.S. application Ser. No. 14/254,844, TOOLS AND INSTRUMENTS FOR USE WITH IMPLANTABLE ENCAPSULATION DEVICES, filed Apr. 16, 2014; and 29/488,209 CASE FOR AN ENCAPSULATION DEVICE, filed Apr. 16, 2014 and U.S. Design application No. 29/488,204, DEPLOYMENT TOOL FOR AN ENCAPSULATION DEVICE, filed Apr. 16, 2014; U.S. Design application No. 29/488,191, SIZING TOOL FOR AN ENCAPSULATION DEVICE, filed Apr. 16, 2014; and U.S. Design application No. 29/488,217, FILL POUCH ASSEMBLY FOR ENCAPSULATION DEVICE, filed Apr. 16, 2014, all of which are incorporated herein in their entireties.

The cell replacement therapy described herein and above in Applicant's prior disclosures relate generally to a macro-encapsulated, implantable, cell product ("combination product") for treatment of diabetes that is not commercially available. Hence, aseptic and semi-automated methods and instruments for loading and filling such an implantable device with cells do not exist except for that described in more detail below.

SUMMARY OF THE INVENTION

Disclosed herein are tools, equipment and/or instruments for aseptically loading and filling an implantable device with cells and sealing the device therein in at least one other sterile container.

In one embodiment, there is provided an aseptic system for loading cells into an implantable device. The system comprises a plurality of components and features for: (i) providing a source for cells and/or therapeutic agent; (ii) a tubing assembly connected to a pump for obtaining the cells and/or therapeutic agent and dispensing the cells and/or therapeutic agent into an implantable device; (iii) at least two components capable of adjusting to at least a first and second position, such position is dependent on the function being performed; and (iv) a sealing means for selectively sealing an implantable device inside a sterile container or package.

In one embodiment, there is provided a cell loading system consisting of a rotatable platform, wherein the rotatable platform further comprises a means for obtaining cells and dispensing said cells into an implantable device. In one embodiment, the means for obtaining the cell comprises a tube assembly. In one embodiment, the rotatable platform is positioned between about 0° to about 180, preferably between 0° to about 90°, preferably at about 90°, preferably at about 45°. In one embodiment, the cell loading system can be manually operated or can be fully or semi-automated. For example, in one embodiment, the cell loading system is semi-automated by detachably connecting the tube assembly to a pump and controlling the pump remotely. In a preferred embodiment, the cell loading system is semi-automated by detachably connecting the tube assembly to to an implantable device port and dispensing the cells in the tube assembly into the device through the port by controlling the pump remotely. In one embodiment, the implantable device comprises a pancreatic type cell. In a preferred embodiment, the implantable device comprises a pancreatic type cell pancreatic progenitor cell.

In one embodiment, there is provided a method for loading an implantable device with cells, the method comprising placing an implantable device with a device port in a compartment wherein the device port is connected to a tubing assembly comprising a reservoir of cells, and wherein the device is detachably coupled to a rotatable platform, and rotating the platform to a position between about 0° to about 180° and dispensing the cells from the tubing assembly into the implantable device, thereby loading the implantable device with the cells. In one embodiment, the implantable device is inside a sterile package. In one embodiment, the implantable device and sterile package are positioned between 45° to 90°. In one embodiment, the device port on the implantable device is sealed by an aseptic means, wherein the means is a source capable of sealing the device port without sealing the sterile package housing the device. In one embodiment, the aseptic means is a radio-frequency (RF) energy source. In one embodiment, the cells being loaded in the implantable device are cell aggregates in suspension. In a preferred embodiment, the cells are pancreatic type cells or pancreatic progenitor cells.

In one embodiment, there is provided a method for expelling residual air from a bag, for example a device case storage bag, the method comprising at least a liquid medium by housing the bag in a first set and a second set of plates, wherein the first set of plates secures the bag and the second set of plates is capable of opening and closing the bag, wherein closing the second plates pushes residual air in the bag out of the bag thereby expelling residual air from the bag. In one embodiment, the device case storage bag and the first set of plates align to secure the bag on the plate.

In one embodiment, there is provided a method for aseptically and selectively sealing a material sensitive to radio frequency (RF) energy, the method comprising placing a first material sensitive to RF energy inside a second material insensitive to RF energy and applying RF energy simultaneously to the first and the second material, wherein the first material sensitive to RF energy seals the material and the second material insensitive to RF energy is not sealed, thereby aseptically and selectively sealing the RF sensitive material. In one embodiment, the RF sensitive material is comprised of a biocompatible polymer selected from a group consisting of polycarbonate-urethane, polyvinyl chloride (PVC), urethane, ethylene vinyl acetate (EVA), polyethylene vinyl acetate (PEVA), acrylonitrile butadiene styrene (ABS), or certain Nylons or polyethylene terephthalates. In another embodiment, the RF insensitive material is comprised of polyethylene terephthalate (trade name is Mylar) or polyester film made from stretched polyethylene terephthalate (PET) or polychlorotrifluoroethylene (PCTFE) fluoropolymer film, high-density polyethylene (HDPE), polystyrene, polyether ether ketone (PEEK), polypropylene, polytetrafluorethylene (PTFE/Teflon), polyethylene, or polymethylmethacrylate, or epoxies, silicone, or parylene.

In one embodiment, there is provided a method for aseptically sealing a device with at least one device port, the method comprising placing a device including at least one port into a sterile container; and sealing the device port in the sterile container selectively while not sealing the sterile container. In one embodiment, sealing the device port comprises RF energy. In another embodiment, sealing the device port comprises a ring or band around the device port. In another embodiment, the sealing ring or the band is crimpable.

In one embodiment, there is provided a method of loading an implantable device with cells, the method comprising loading a tube assembly with at least a first a flushing volume, cells volume and a priming volume; and dispensing first the priming volume, cells volume and priming volume from the tube assembly into the implantable device, thereby loading an implantable device with cells.

Other embodiments of the present inventions are described with reference to the list of numbered paragraphs below:

1. A cell loading system comprising a rotatable platform, wherein the rotatable platform further comprises a means for obtaining cells and dispensing said cells into an implantable device.
2. The cell loading system of claim 1, wherein the system further comprises a tube assembly wherein the tube assembly is a cell reservoir comprising a cell dose volume.
3. The cell loading system of claim 1, wherein the rotatable platform is positioned between about 0° to about 180°.
4. The cell loading system of claim 1, wherein the rotatable platform is positioned between about 0° to about 90°.
5. The cell loading system of claim 1, wherein the rotatable platform is positioned at about 90°.
6. The cell loading system of claim 1, wherein the rotatable platform is positioned at about 45°.
7. The cell loading system of claim 1, wherein the system is manual, fully or semi-automated.
8. The cell loading system of claim 7, wherein the system is automated by detachably connecting the tube assembly to a pump and controlling the pump.
9. The cell loading system of claim 8, wherein the tube assembly is detachably connected to an implantable device port and the pump dispenses the cells in tubing assembly into the device through the port.
10. The cell loading system of claim 1, wherein the cell is a pancreatic type cell.
11. The cell loading system of claim 10, wherein the cell is a pancreatic progenitor cell.
12. A method of loading an implantable device with cells comprising:
    a. Placing an implantable device with a device port in a compartment wherein the device port is connected to a tubing assembly comprising a reservoir of cells, and wherein the device is detachably coupled to a rotatable platform;
    b. Rotating the platform to a position between about 0° to about 180°;
    c. Dispensing the cells from the tubing assembly into the implantable device, thereby loading the implantable device with the cells. 0"
13. The method of claim 12, wherein the device is inside a sterile package.
14. The method of claim 13, wherein the device and package are on the rotatable platform and is positioned between 45° to 90°.
15. The method of claim 14, wherein the device port is sealed by an aseptic means.
16. The method of claim 15, wherein the aseptic means selectively seals the device port and not the sterile package outside the device.
17. The method of claim 15, wherein the aseptic means is RF sealing.
18. The method of claim 12, wherein the cells are cell aggregates in suspension.
19. The method of claim 12, wherein the cells are pancreatic type cells.
20. A method for expelling residual air from a bag comprising at least a liquid medium, the method comprising: providing a first set of plates and a second set of plates, wherein the first set of plates secures the bag and the second set of plates is capable of opening and closing the bag, wherein closing the second plates pushes residual air in the bag out of the bag thereby expelling residual air from the bag.

21. The method of claim 20, wherein the bag and the first set of plates align to secure the bag on the plate.

22. A method for aseptically and selectively sealing a material sensitive to radio frequency (RF) energy, the method comprising:
   a. Placing a first material sensitive to RF energy inside a second material insensitive to RF energy
   b. Applying RF energy simultaneously to the first and the second material, wherein the first material sensitive to RF energy seals the material and the second material insensitive to RF energy is not sealed, thereby aseptically and selectively sealing the RF sensitive material.

23. The method of claim 22, wherein the RF sensitive material is comprised of a biocompatible polymer selected from a group consisting of polycarbonate-urethane, polyvinyl chloride (PVC), urethane, ethylene vinyl acetate (EVA), polyethylene vinyl acetate (PEVA), acrylonitrile butadiene styrene (ABS), or certain Nylons or polyethylene terephthalates.

24. The method of claim 21, wherein the RF insensitive material is comprised of polyethylene terephthalate (trade name is Mylar) or polyester film made from stretched polyethylene terephthalate (PET) or polychlorotrifluoroethylene (PCTFE) fluoropolymer film, high-density polyethylene (HDPE), polystyrene, polyether ether ketone (PEEK), polypropylene, polytetrafluorethylene (PTFE/Teflon), polyethylene, or polymethylmethacrylate or, epoxies, silicone, or parylene.

25. A method for aseptically sealing a device with at least one device port comprising:
   a. Placing a device comprising at least one port into a sterile container; and
   b. Sealing the device port in the sterile container selectively while not sealing the sterile container.

26. The method of claim 25, further comprising RF energy for sealing the device port.

27. The method of claim 25, further comprising a sealing ring or band around the device port.

28. The method of claim 27, wherein the sealing ring or band is crimpable.

29. A method of loading an implantable device with cells comprising:
   (a) Loading a tube assembly with at least a first a flushing volume, cells volume and a priming volume; and
   (b) Dispensing first the priming volume, cells volume and priming volume from step (a) and into the implantable device, thereby loading an implantable device with cells.

The foregoing and additional embodiments, features and advantages of the invention are disclosed and will be apparent from the following, more particular description of the preferred embodiments of the invention, the accompanying drawings, and the claims.

BRIEF DESCRIPTION OF THE DRAWINGS

For a more complete understanding of the embodiments of the invention, and the advantages thereof, reference is now made to the ensuing descriptions taken in connection with the accompanying drawings briefly described as follows:

FIG. 11 is a flowchart showing the comprehensive steps for sealing the device, storing and sealing the device case storage bag and sealing the shipping bag, according to an embodiment of the invention.

DETAILED DESCRIPTION OF EMBODIMENTS

Figures 1A, 1B:
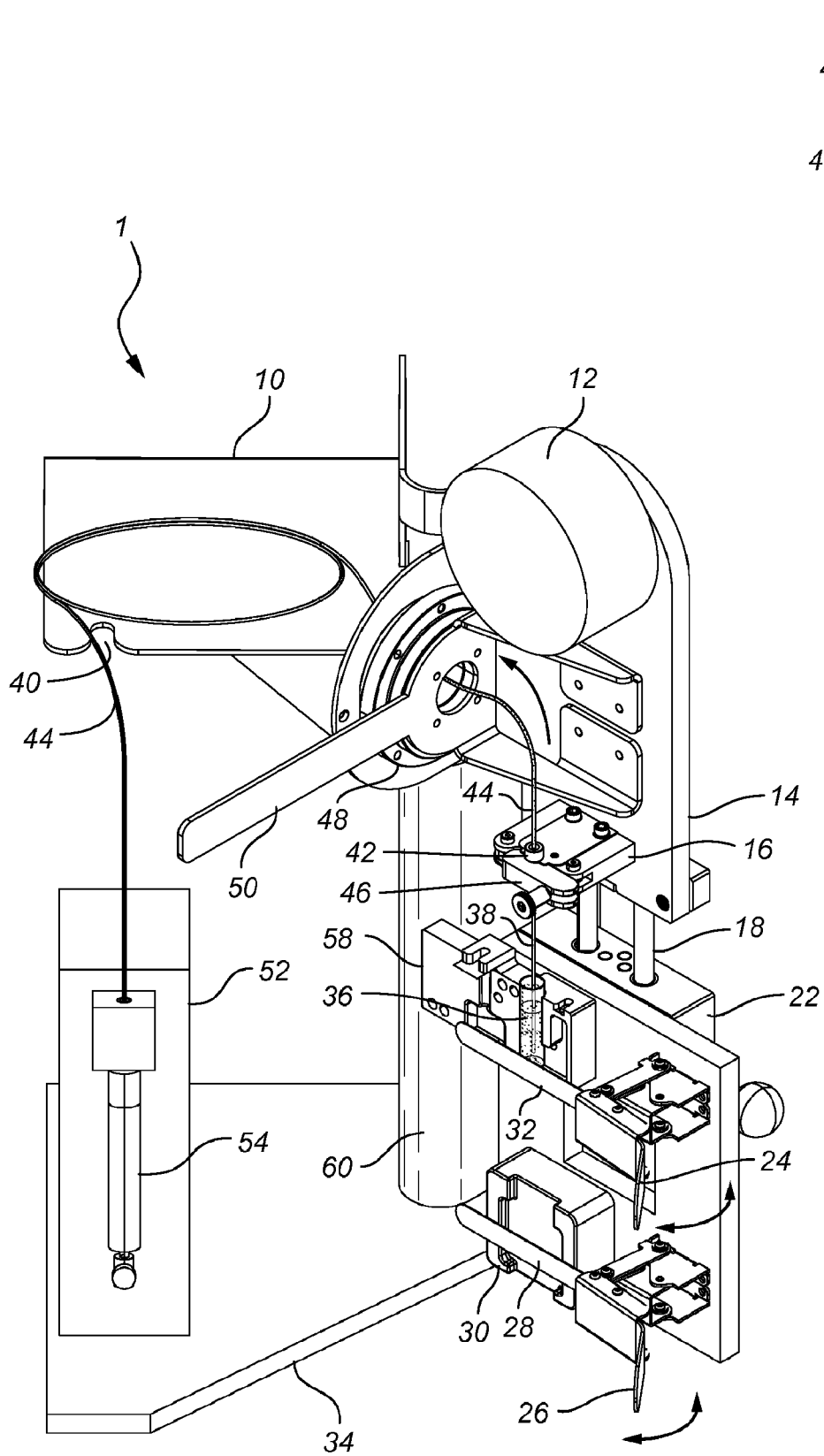
FIG. 1 illustrates a perspective view of a priming and cell loading system wherein the assembly consists of a syringe and syringe pump, a dosing tube assembly, a rotatable platform detachably connected to an flexplate mount, a multi-position block capable of housing a cell source (vial) and a device fill pouch assembly (DFPA), a DFPA nesting block, and a sliding carriage having connected the multi-position block and the DFPA nesting block, and the rotatable platform is capable of rotating between 0 and 180 degrees.

Further features and advantages of the invention, as well as the structure and operation of various embodiments of the invention, are described in detail below with reference to the accompanying FIGS. 1-11, whereby like reference numerals refer to like elements and is not limited to the elements described in the drawings or in the embodiments.

Although embodiments of the invention are described in the context of implantable devices with pancreatic progenitor cells and/or immature beta cells, one of ordinary skill in the art readily appreciates that the present invention is applicable for macro-encapsulation of any type of cells including cell aggregate suspensions, therapeutic agents, or mixtures thereof, including but not limited to thyroid cells, parathyroid cells, pancreatic cells, intestinal cells, thymus cells, hepatic cells, endocrine cells, skin cells, hematopoietic cells, bone marrow stem cells, renal cells, muscle cells, neural cells, stem cells, embryonic stem cells, lineage-restricted cells, progenitor cells, precursor cells, genetically engineered cells, tumor cells, and derivatives and combinations thereof for the treatment of one or more disease or disorder, including, but not limited to diabetes mellitus. Also contemplated are cells producing cell-based products such as proteins (e.g. hormones and/or other proteins deficient in human diseases and the like), antibodies, antibiotics, lymphokines and the like for therapeutic indications. One of ordinary skill in the art can also appreciate that the present embodiments are applicable to different implantable device types, materials, sizes, and/or configurations.

As used herein, the term "device" or "implantable device" refers to any macro-encapsulation or cell-encapsulation device capable for use in priming and loading as described herein, including but not limited to an implantable device, according to embodiments of the invention, including but not limited to Applicants PCT/US2014/022109 application, titled 3-DIMENSIONAL LARGE CAPACITY CELL ENCAPSULATION DEVICE, filed Mar. 7, 2014; and U.S. Design application Nos. 29/408,366 filed Dec. 12, 2011; 29/408,368 filed Dec. 12, 2011; 29/423,365 filed May 31, 2012; 29/447,944 filed Mar. 13, 2013; 29/484,363, 29/484,359, 29/484,360, 29/484,357, 29/484,356, 29/484,355, 29/484,362 and 29/484,35, filed Mar. 7, 2014.

As used herein, the term "case" or "cage" or "device case" or "device cage" 74 refers to any container capable of housing a device. The case can be used for example when priming and loading the device and sealing the device port to maintain the integrity and sterility of the device, according to embodiments of the invention, including but not limited to an implantable device as described in Applicants PCT/US2014/034425, TOOLS AND INSTRUMENTS FOR USE WITH IMPLANTABLE ENCAPSULATION DEVICES, filed Apr. 16, 2014; and U.S. Design application No. 29/488,217, FILL POUCH ASSEMBLY FOR ENCAPSULATION DEVICE, filed Apr. 16, 2014; and 29/488,209 CASE FOR AN ENCAPSULATION DEVICE, filed Apr. 16, 2014.

As used herein, the term "fill pouch", "device fill pouch", or "device fill pouch assembly" or "DFPA" 62 refers to any container or pouch capable of housing a device and case, The DFPA can be used for example when priming and loading the device and sealing the device to maintain the integrity and sterility of the case and the device, according to embodiments of the invention, including but not limited to Applicants PCT/US2014/034425, TOOLS AND INSTRUMENTS FOR USE WITH IMPLANTABLE ENCAPSULATION DEVICES, filed Apr. 16, 2014; and U.S. Design application No. 29/488,217, FILL POUCH ASSEMBLY FOR ENCAPSULATION DEVICE, filed Apr. 16, 2014.

As used herein, the term "device case storage bag" or "storage bag" 124 refers to any bag or pouch or sterilizable bag or pouch capable of housing a device case and device therein for sealing, according to embodiments of the invention, including but not limited to a storage bag as described in Applicants PCT/US2014/034425, TOOLS AND INSTRUMENTS FOR USE WITH IMPLANTABLE ENCAPSULATION DEVICES, filed Apr. 16, 2014. Typically the device case storage bag 124 will have a RF-reactive portion.

As used herein, the term "shipping bag", "shipping package" or "shipping pouch" 126 refers to any bag or pouch or sterilizable bag or pouch capable of housing multiple items including but not limited to a device case storage bag, device case and device therein for sealing, according to embodiments of the invention, including but not limited to a shipping bag as described in Applicants PCT/US2014/034425, TOOLS AND INSTRUMENTS FOR USE WITH IMPLANTABLE ENCAPSULATION DEVICES, filed Apr. 16, 2014.

As used herein, the terms "assembly", "system", "fixture", "apparatus", "component" "platform" and/or "means" 1, 2, 68, 76 are interchangeable and are used interchangeably, according to embodiments of the invention.

As used herein, the term "adjustable", "moveable" or "multi-position" 14, 22, 58, 106 refers to a component capable of but not limited to moving laterally, vertically or rotate in different positions from zero (0) to one-hundred eighty (180) degrees or more, or have open, semi-opened, semi-closed or closed configurations and any means for achieving these configurations, according to embodiments of the invention.

As used herein, the term "fluidic reservoir", "cell reservoir", "cell source", "cell container" and/or "aliquot vial" 36 refers to a tubing or container capable of storing and holding cells according to embodiments of the invention.

As used herein, the term "cell", "cells", "cell aggregate" or "cell aggregates" may be used interchangeably depending on their context, but it is not intended to limit the various embodiments to such, as the priming and loading system embodiments described herein may be utilized for different types of cell courses in different formats, not just as aggregates.

As used herein, the term "pancreatic endoderm cell", "PDX1-positive pancreatic endoderm", "PEC", and "pancreatic progenitors" refer to a therapeutic cell source, according to embodiments of the invention, including but not limited to Applicants U.S. application Ser. No. 12/099,759, entitled METHODS OF PRODUCING PANCREATIC HORMONES, filed Apr. 8, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. No. 14/106,330, entitled IN VITRO DIFFERENTIATION OF PLURIPOTENT STEM CELLS TO PANCREATIC ENDODERM CELLS (PEC) AND IMMATURE BETA CELLS, filed Dec. 12, 2013; Ser. No. 14/201,630, filed Mar. 7, 2014; and PCT/US2014/026529, IN VITRO DIFFERENTIATION OF PLURIPOTENT STEM CELLS TO PANCREATIC ENDODERM CELLS (PEC) AND ENDOCRINE CELLS, filed Mar. 13, 2014;

As used herein "cell loading system" or "priming and cell loading system" or "loading system" means any system for loading a device with a therapeutic agent or cells.

As used herein "dose tube platform" or "tubing mount" means any platform or mount that provides a means for keeping a tubing assembly held on the mount.

As used herein "device loading port" or "device loading tube" or "device port" or "device tube" means any tube for priming or loading agents and/or cells into a device and later sealed.

As used herein, "radio frequency", "electromagnetic energy" or equivalents thereof are a means of selectively sealing certain thermoplastic film materials while not others.

As used herein, "cell dose" or "dose" generally, is a reference any number of cells or cell aggregates or therapeutic agents. For example, a cell container or vial may have 1 to $10^6$, $10^7$, $10^9$ or more cells, however, for purposes of the these embodiments any said amount in one cell vial is referred to as one cell dose, and does not indicate the number of cells. The priming and cell loading system 1 has tested small and large cell volumes without incident, so the system 1 can accommodate different volumes and therefore many cell doses. In one embodiment, the system 1 can be programmed to store 1, 2, 3, 4, 5 etc. cell doses depending on the number of cell doses necessary for the treatment and/or necessary to fill a particular sized device or multiple devices per manufacturing run. Determining the volume of cells for one cell dose and that of multiple cell doses for this system does not require additional invention but is well within the skill of one in the art.

As used herein, "coupling system", "attachment system", "closing system", "locking system", "latching system" or equivalents thereof refers to any means for attaching, coupling, connecting or latching one or more components such as a hinge, snap, button, string, hook, latch, fasteners, clips, clamps, nuts, bolts or other types of fasteners used to detachably or permanently connect components or fixtures together.

As used herein, certain components or parts are closed or open by describing use of latches or cam levers being pulled or pushed (e.g. being pushed downward or pulled upward), which is not material to the closing or opening of the component because it is possible that either motion (pulling or pushing) will perform either function (opening or closing).

As used herein, the term "loaded" is a reference to filling or putting something into something else, e.g. filling or loading a device, or filling or loading a dose tubing assembly.

Implantable Device

Although not the object of the present embodiments, an implantable device is described and illustrated throughout the application. For example, FIGS. 2, 3, 4, 5, 6 & 8 illustrate a device case 74 with an implantable device 200 secured inside. However, the embodiments described herein are not limited to these implantable devices but are possible with other implantable or non-implantable devices. One skilled in the art can modify the priming and cell loading system 1 described herein for other devices without departing from the general embodiments. Applicants have described various planar and non-planar (e.g. 3-dimensional) implantable devices that are contemplated including but not limited to self-expanding implantable devices, large capacity or macro-encapsulation, planar and non-planar implantable devices, or 3-dimensional macro-encapsulation implantable devices. Other encapsulation implantable devices have been described by Applicant, for example, PCT/US2014/022109, 3-DIMENSIONAL LARGE CAPACITY CELL ENCAPSULATION DEVICE, filed Mar. 7, 2014; and U.S. Design application Nos. 29/408,366 filed Dec. 12, 2011; 29/408,368 filed Dec. 12, 2011; 29/423, 365 filed May 31, 2012; 29/447,944 filed Mar. 13, 2013; 29/484,363, 29/484,359, 29/484,360, 29/484,357; 29/484, 356, 29/484,355, 29/484,362 and 29/484,35, titled 3-DIMENSIONAL LARGE CAPACITY CELL ENCAPSULATION DEVICE and filed Mar. 7, 2014.

Therapeutic Cells and Agents

The embodiments herein describe priming and loading therapeutic cells and therapeutic agents into implantable devices. In particular, therapeutic cells and agents that consist of cell aggregate suspensions. Applicants are developing a cell therapy for diabetes, specifically an encapsulated cell therapy to treat diabetes, and have described in detail various endoderm-lineage or definitive-endoderm lineage cells, specifically pancreatic-lineage cells for use with the embodiments described herein. For example, Applicants have described in detail mesendoderm and definitive endoderm-lineage type cells in at least U.S. application Ser. No. 12/099,759, entitled METHODS OF PRODUCING PANCREATIC HORMONES, filed Apr. 8, 2008; Ser. No. 12/618,659, entitled ENCAPSULATION OF PANCREATIC LINEAGE CELLS DERIVED FROM HUMAN PLURIPOTENT STEM CELLS, filed Nov. 13, 2009; Ser. No. 14/106,330, entitled IN VITRO DIFFERENTIATION OF PLURIPOTENT STEM CELLS TO PANCREATIC ENDODERM CELLS (PEC) AND IMMATURE BETA CELLS, filed Dec. 12, 2013; Ser. No. 14/201,630, filed Mar. 7, 2014; and PCT/US2014/026529, IN VITRO DIFFERENTIATION OF PLURIPOTENT STEM CELLS TO PANCREATIC ENDODERM CELLS (PEC) AND ENDOCRINE CELLS, filed Mar. 13, 2014. In one preferred embodiment, the implantable device consists of a therapeutic agent, living cells, endoderm-lineage cells, definitive endoderm-lineage cells, pancreatic progenitor cells, pancreatic progenitor cells differentiated from pluripotent cells (such as human embryonic stem cells including those derived from methods now known or to be discovered in the future including derivation using non-destruction of a human embryo or fetus, cord blood stem cells, induced pluripotent stem cells, reprogrammed cells, parthenote cells, gonadal germ cells, and mesenchymal, or hematopoietic stem cells), a PDX-1 positive pancreatic progenitor cell, an endocrine precursor cell, an endocrine cell, an immature beta cell, an immature islet cell, and the like.

Various publications including scientific journal articles, patent publications and patents are herein referred to and the disclosure of each of them is incorporated by reference in its entirety. For example, instruments and methods for making pancreatic progenitor populations and/or immature beta cell populations, sterilizing, storing, securing and transferring the devices, sizing and preparing the anatomical site, delivering and deploying the combination product at the implantation site, maturing and making functional hormone secreting cells in vivo are disclosed in Applicant's above described patent applications and are incorporated herein by reference in their entirety.

Priming & Loading System

Figure 2A:
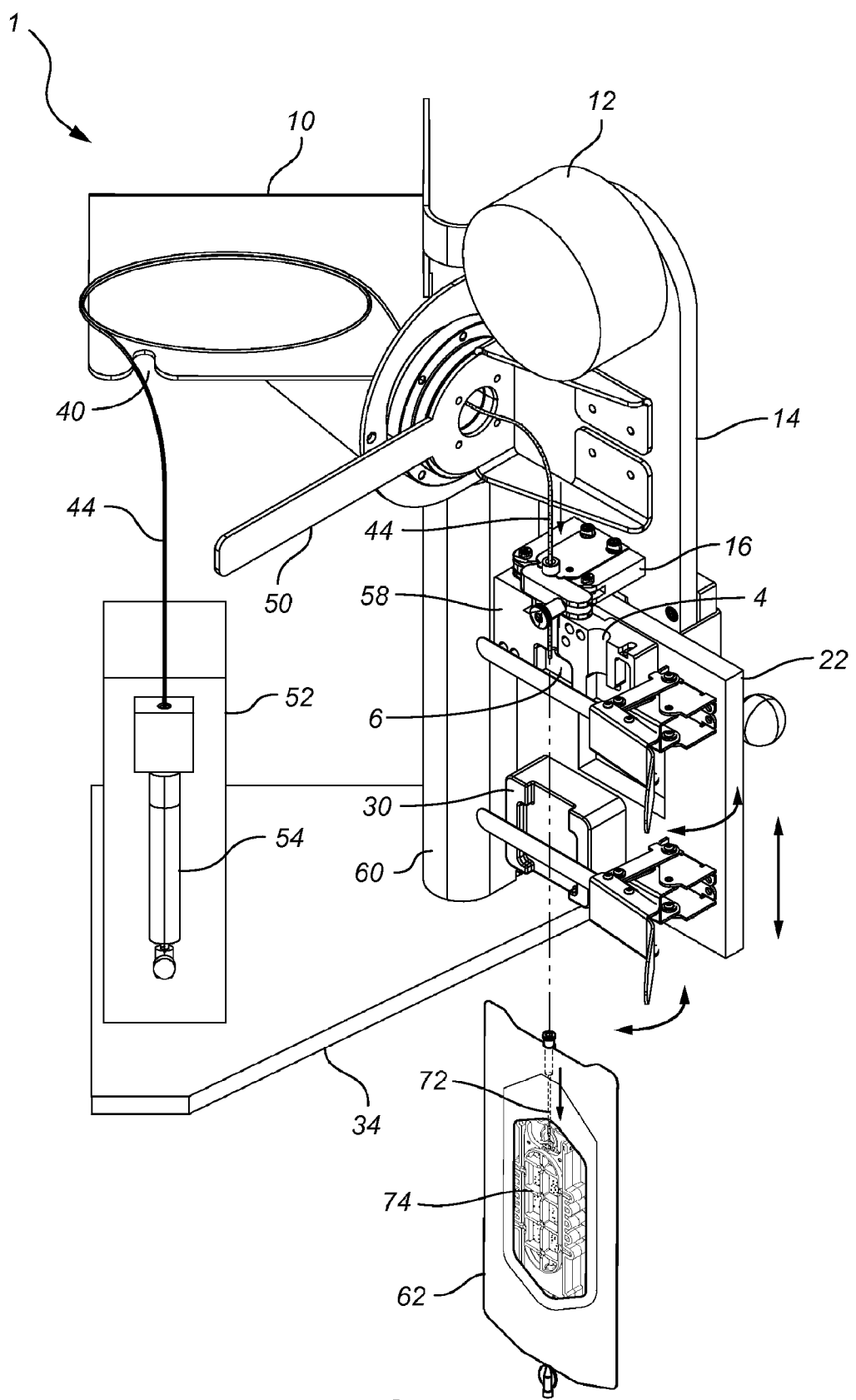
FIGS. 2A & B illustrate a perspective view of a priming and cell loading system wherein the dashed lines show where the DFPA with a device case and implantable device therein would reside during priming and loading (A); and a device case with an implantable device therein (B), according to an embodiment of the invention.
Figure 2B:
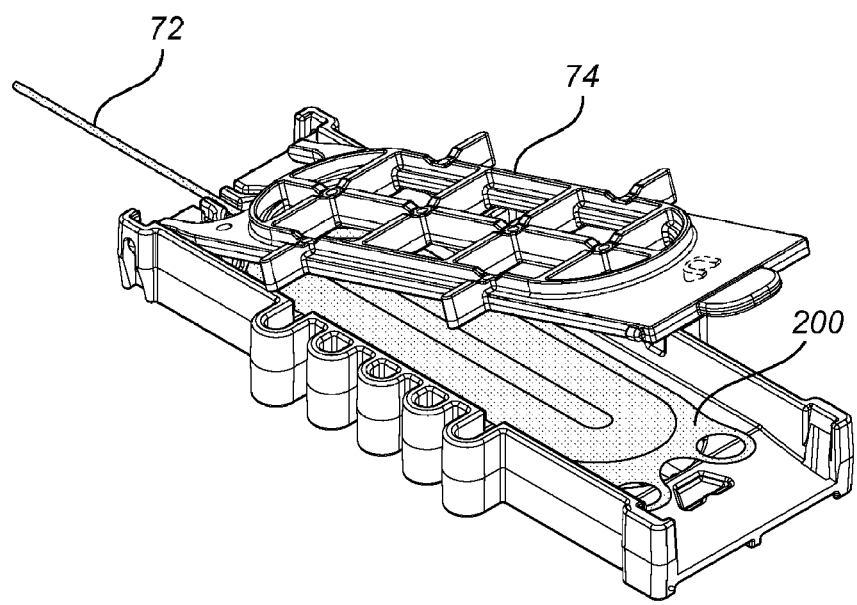
Figure 3:
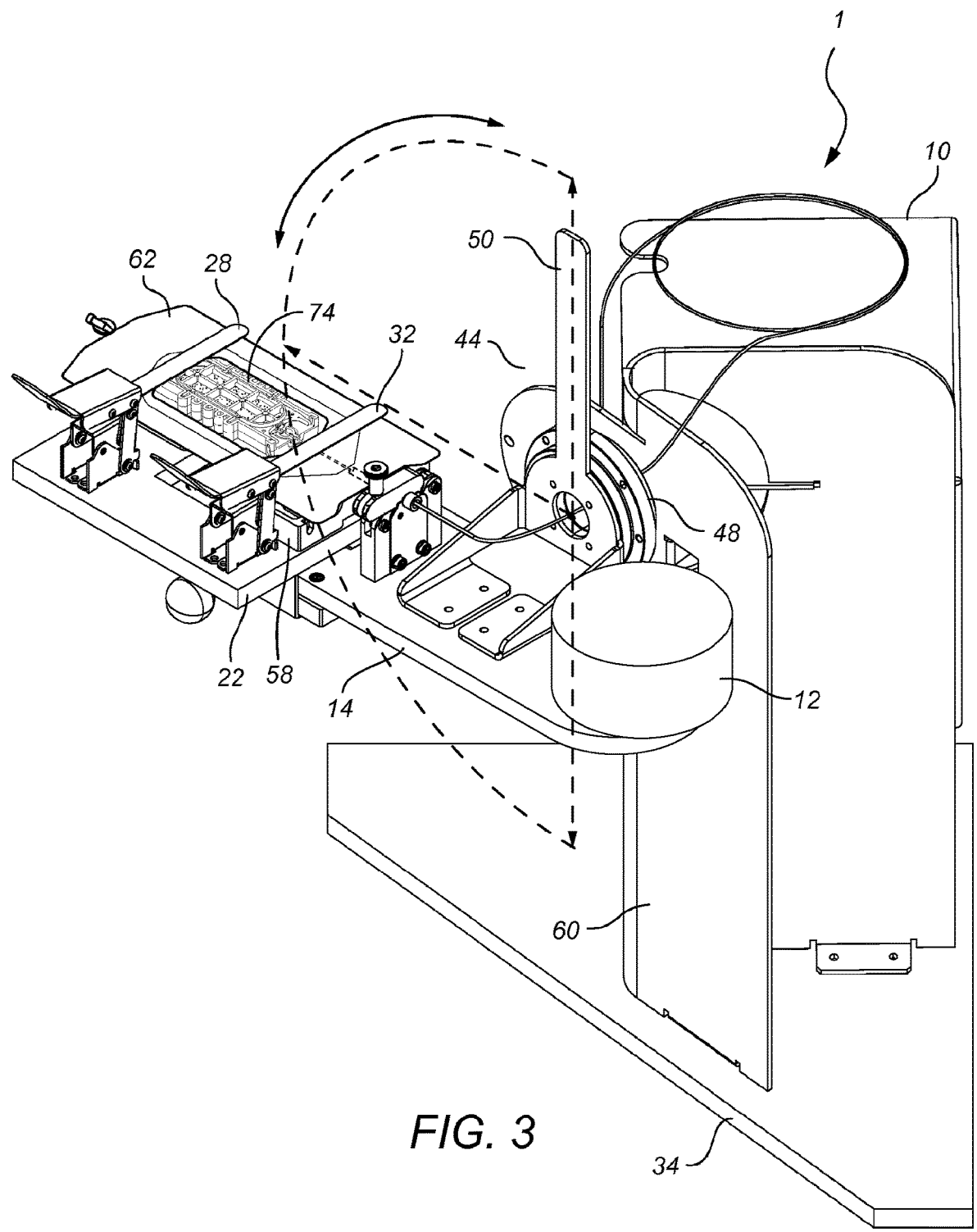
FIG. 3 illustrates a perspective side view of a priming and cell loading system wherein the rotatable platform is rotated and positioned 90 degrees from the base, according to an embodiment of the invention.

FIGS. 1-3 illustrate a nonlimiting, nonexclusive embodiment of a system 1 for priming and loading cells (or any fluid suspension including therapeutic agents) into an implantable device. The system 1 is constructed with various features to perform at least the following functions: (i) Loading the fluidic reservoir 44 and dosing tube 38 (collectively the dosing tube assembly 44, 38); (ii) Capturing the cell vial 36 and DFPA 62 that contains the device case 74 and device 200 therein for loading the dosing tube assembly 44, 38 and the device 200 inside the DFPA 62, respectively; (iii) Priming, loading or filling the cells and flushing the cells into the device; all (functions i, ii, and iii) in a controlled, aseptic, manual, semi-automated and/or automated fashion.

FIGS. 1-3 illustrate non-limiting, non-exclusive embodiments of the invention including: a syringe 54 and syringe pump 52; a dosing tube platform 10; a fluidic reservoir 44 and dosing tube 38; a rotatable platform 14 having a flex-plate mount 16, rotating handle 50 connected to a rotating bearing 48, and a counter weight 12; an adjustable sliding carriage 22 with an adjustable multi-position block 58 with a first vial 4 position and a second DFPA position 6 and a DFPA nesting block 30; all components are connected to a frame 60 (dose tubing platform 10, rotatable platform 14 and sliding carriage 22), which is mounted on a base 34. Specific embodiments are discussed in more detail below.

The priming and cell loading system 1 is also referred to a "cell loader", "cell loader system", or "cell filling assembly" or equivalents thereof. In any embodiment, the priming and cell loading system 1 performs its function in an aseptic manner, whereby the integrity and sterility of the various components of the system and/or components used with the system are maintained. In one embodiment, all the systems, components, means and methods described herein are performed in a Good Manufacturing Practice (GMP) appropriate clean rooms and according to at least U.S. and European regulatory agencies.

Additional components can be added to the priming and cell loading system 1, for example, external sensors such as a cell counter, pressure transducer, heat sensor, velocity sensor and the like.

Dosing Tube Assembly

For sterility assurance, a disposable dosing tube assembly 44, 38 comprising a fluidic reservoir 44 and a dosing tube 38 is connected to a syringe 54, and further connected to a syringe pump 52. The dosing tube 38 can also be referred to as a loading tube 38. The fluidic reservoir 44 is used to hold liquid medium for priming the device 200, storing the cell aggregates or liquid medium for flushing the cell aggregates into the device 200. In one embodiment, there is also a fitting 42 separating the fluidic reservoir 44 and the dosing tube 38, and this is connected to the syringe and they are sterilized together as one unit. This sterile unit is then connected to the syringe pump 52. In one embodiment, the dosing tube assembly 44, 38 is a uniform-diameter tube. The diameter of the tube was selected to ease connections between various components of the priming and cell loading system 1 (e.g., connections to the syringe 54, to the flexplate mount 16, and to the device port 72). Utilizing a constant diameter tube throughout eliminates the number of transitions and additional fittings or valves, which are otherwise required if there are changes in the tubing size (diameter). For example, when tubing diameter changes, fittings or valves are used to accommodate the change in the size of the tubing, this change provides opportunities for cells, especially suspension aggregates to become clogged, potentially at different areas in the tubing system, or to become trapped in the fittings during transport (e.g. cell aggregates may settle in small grooves of a fitting and affect movement of other cell aggregates) or they may get destroyed by shearing, especially if they are transitioning to a smaller diameter tubing. Hence, maintaining a consistent diameter for the tubing system is advantageous because it reduces the potential for the cell aggregates to get trapped near or in the connections or fittings. A constant diameter tube also enables responsive fluidic volume movement when using a liquid pumping medium including but not limited to sterile phosphate buffered saline ("PBS", or "saline"), stem cell media, and the like. A fluidic reservoir 44 with fewer fittings 42 and/or valves also permits a gentler transport of mechanically sensitive material, in particular shear-sensitive biological material including but not limited to living animal, human and/or plant cells, viruses, agglomerates of protein precipitates, protein crystals, native proteins, antibodies, liposomes and cell aggregates in suspension. Fewer fittings also reduce possible contamination and maintain a sterile, aseptic environment, particularly for human use. In one embodiment, additional fittings can be avoided in the dosing tubing 38 by using a smaller radius tube than the device port 72 such that the dosing tube 38 can be directly inserted into the device port 72 to load cells, and potentially preventing contamination of the dosing tube 38 and/or the device port 72 and device 200 therein.

Various sizes, diameters, lengths, tapers, bulbs, balloons and other features of the fluidic reservoir 44 are possible and may depend on the material to be aspirated and loaded and/or the device to receive such material. The tip of the dosing tube 38 is connected to the device port 72 of the implantable device 200, so for all the same reasons as described above the dosing tube 38 should be about the same diameter as the device port 72.

In one embodiment, liquid saline is used as a pumping fluid in the dosing tube assembly 44, 38. This is advantageous because more control can be used with a pumping fluid versus that of pumping air through the tube assembly. Additionally, the regulatory compliance when using air is more onerous and burdensome than that for a liquid pumping fluid.

In one embodiment, the length of the tube selected depends in part on the maximum volume of media and cell aggregates for loading the largest capacity device. For example, a tube length of about 20 feet is capable of holding about 5 mL of total tube volume for loading at least an EN250 device (about 250 µL).

In one embodiment, the fluidic reservoir 44 can be mounted or held on a dosing tube platform 10 or contained by other means known in the art.

Tubing Platform

A dosing tube platform 10 provides a means for keeping or holding the dosing tubing 44, 38 and in particular the fluidic reservoir 44, for example, longer dosing tubing can be coiled and held on the mount 10. The mount 10 maintains the fluidic reservoir 44 in a horizontal orientation to prevent air bubbles from forming within the tubing as fluid and air are being passed through via the syringe pump 52. For example, if the fluidic reservoir 44 were to achieve a more vertical position (instead of being horizontal), the leading flow front of the following media can run under the air bolus and create an air bubble. Keeping the tubing horizontal prevents this.

In one embodiment, the dosing tube platform 10 can further consist of a cylindrical recess 40, a pivoting retaining latch, and/or a securing thumbscrew to secure the tubing and/or maintain it in the appropriate position.

Syringe & Syringe Pump

Typical surgical (manual) syringes employ a piston and cylinder and are suitable for pumping (dispensing) measured small amounts of fluid for everyday laboratory research use. For example, Applicants have described use of Hamilton syringes to measure small amounts of pancreatic progenitors and loading them into implantable devices for implantation. See at least U.S. application Ser. No. 12/099,759, entitled METHODS OF PRODUCING PANCREATIC HORMONES, filed Apr. 8, 2008; and Ser. No. 12/618,659, entitled ENCAPSULATION OF PANCREATIC LINEAGE CELLS DERIVED FROM HUMAN PLURIPOTENT STEM CELLS, filed Nov. 13, 2009. However, for a commercial therapy requiring priming and filling many and multiple devices, or larger devices, or 3-dimensional devices, a manual, hand-held syringe loading is not conducive for this scaling-up purpose. Hence, there is a need for an automated or semi-automated system capable of priming and loading (dispensing) many dose volumes with precision and accuracy, while maintaining cell viability (e.g. reduce shear stress).

FIGS. 1-2 illustrate a nonlimiting, nonexclusive embodiment of a syringe 54 and syringe pump 52. They are commercially available from various manufacturers including but not limited to Cavro, Parker, Kloehn and Hamilton and the like.

Pumps can be utilized with various sized syringes for dispensing volumes in the range of 1 microliter to 50 milliliter. Syringe pumps are generally comprised of a syringe barrel, inlet and outlet valves, a piston and a motor. In one embodiment, the syringe barrel plugs directly into the valve, and using seals, the valve can be essentially separate from the syringe. In this instance, the syringe area and the piston linear displacement define the dispensed syringe fluid volume. In another embodiment, syringe pumps can consist of a piston and cylinder, in which case the piston can also provide the valving functions. In a preferred embodiment, the syringe barrel plugs directly into a fitting (in place of a valve), and using seals, the fitting can be essentially separate from the syringe. Still, in another embodiment, a motor (e.g. a stepper motor) is used to control (or move) the syringe piston displacement.

In a preferred embodiment, a Norgren Kloehn Versapump ("the Kloehn pump"), was utilized for aspirating and dispensing pancreatic progenitor cell aggregate suspensions (or PEC), Applicant's candidate cell product. The pump is powered by a 24 VDC power brick and consists of a stepper motor precision syringe pump, available in 12000, 24000 or 48000 steps per full stroke. Full stroke of the pump is about 6 cm (60 mm). Various sizes of syringes can be installed with the pump, from as small as 25 µL to as large as 50 mL. Aspiration and dispensing volume accurately is determined by syringe volume and steps per stroke, with greater accuracy achieved with smaller capacity syringes. In one embodiment, cell loading EN250 (maximum capacity of about 250 µL) and EN20 (maximum capacity of about 20 µL) devices can be accomplished using a 10 mL syringe with about 48000 steps per full stroke pump. The nominal fluidic volume resolution achieved with this combination is about 0.2 µL/step. For example, 10 mL syringes from Zinsser North America (N.A.) can be used to load EN250 and EN20 devices.

Syringe Pump Controls

A computer can be used to communicate with the syringe pump 52 for the various aspirations (pull, negative pressure), dwell and dispense (positive pressure) commands. The Kloehn pump for example features command sets with many capabilities, and various command strings are stored in the controller software application and sent to the pump 52 upon user demand Responses from the pump 52 are received and displayed in the controller application.

In another embodiment, the pump 52 can store its commands internally (on-board non-volatile RAM) and execute them via hardware inputs, so a simple push button interface is possible to command the syringe pump 52 to aspirate, dwell, and dispense as necessary.

In another embodiment, the syringe pump 52 can receive hardware inputs from an integrated assembly machine control system. Using a computer was selected for convenience; however, any automated or manual method for aspirating, dwelling and dispensing fluids or cells, in particular, cell suspension aggregates, is reasonable for one skilled in the art.

Rotatable Platform

A unique feature of the priming and loading system 1 is the rotatable platform 14, which is connected to the sliding carriage 22 (described in more detail below) and together both can be rotated from 0 to 180 degrees. The rotatable platform 14 can further consist of a flexplate mount 16 (described in more detail below). The rotatable platform 14 can be rotated through 180° of motion, from vertically downwards through vertically upwards using a rotating handle 50 that moves around a rotating bearing 48, which is attached to the frame 60 and base 34 of the priming and cell loading system 1. See FIG. 3 showing the side perspective of the priming and cell loading system 1. FIG. 3 also shows the rotating platform 14 and sliding carriage 22 rotated at about 90 degrees relative to the base. To fix or clamp the rotatable platform 14 into the desired position, the rotating bearing 48 can be secured by one or more locknuts. In other embodiments, alternate securing or locking mechanisms including but not limited to toggle clamps, friction clutches, ratchets and the like are also possible to secure the position of the rotatable platform 14.

In one embodiment, to remove and install a vial 36 and/or a DFPA 62, the rotatable platform 14 is oriented vertically downwards, similar to that illustrated in FIGS. 1&2. For smaller devices (e.g. device with maximum capacity of 20 µL such as an EN20 device) wetting or priming may be achieved at a variety of orientation angles. For larger devices (e.g. device with maximum capacity of 250 µL such as an EN250 device) wetting or priming is more efficient if the rotatable platform is oriented vertically upward, more similar to that in FIG. 3. It is within the knowledge of one skilled in art to optimize and vary the position of the rotatable platform 14 for loading a desired device, for example, certain devices load well with the rotatable platform 14 oriented horizontally, while others load better when oriented upwards whereby the rotatable platform 14 is at an angle between 180° and 90° for example. Varying the angle of rotation for dispensing and loading the devices will also assist in a more even distribution of the cells inside the device chamber and may reduce the number of air bubbles or pockets which may form. Air bubbles or pockets trapped inside the device may negatively affect the ability of the device to receive cell aggregates; and this in turn may negatively affect the cell distribution in the device, which in turn may affect cell growth, proliferation, maturation and development at or near the site of the bubble. Thus, avoidance of creating bubbles is critical for good (even) cell distribution and a rotatable platform 14 may facilitate this by being able to easily manipulate with small or large movements affecting orientation.

In one embodiment, due to the weight components such as the multi-position block 58 and the DFPA nesting block 30, the rotatable platform 14 may have a counter-weight 12 at the proximal portion of the platform 14 for stability.

Flexplate Mount

A flexplate mount 16 functions to positions the dosing tubing 38 at the center of the vial 36 when presented, and aligns the dosing tubing 38 with the device port 72 when presented. The flexplate may flex slightly and applies a constant force to maintain a closed connection between the dosing tubing 38 and the device port 72 fittings inside the DFPA 62 when fully engaged. In one embodiment, the flexplate mount 16 can accommodate a fluidic reservoir tubing 44 and dosing tubing 38 of different sizes by choice of fitting 42.

In one embodiment, simultaneous or synchronous loading of one or more devices can be accommodated by adding one or more dosing tube assemblies 44,38, one or more fittings 42, and on ore more latches 46. Hence, the flexplate mount 16 can be adjusted or optimized to perform a number of priming and loading functions. Such modifications to the flexplate mount 16 can be accomplished by one of ordinary skill in the art.

In one embodiment, multiple dosing tubing systems 44, 38 can be employed with multiple fittings 42, but loaded simultaneously or synchronously into the same or different devices.

Figure 10:
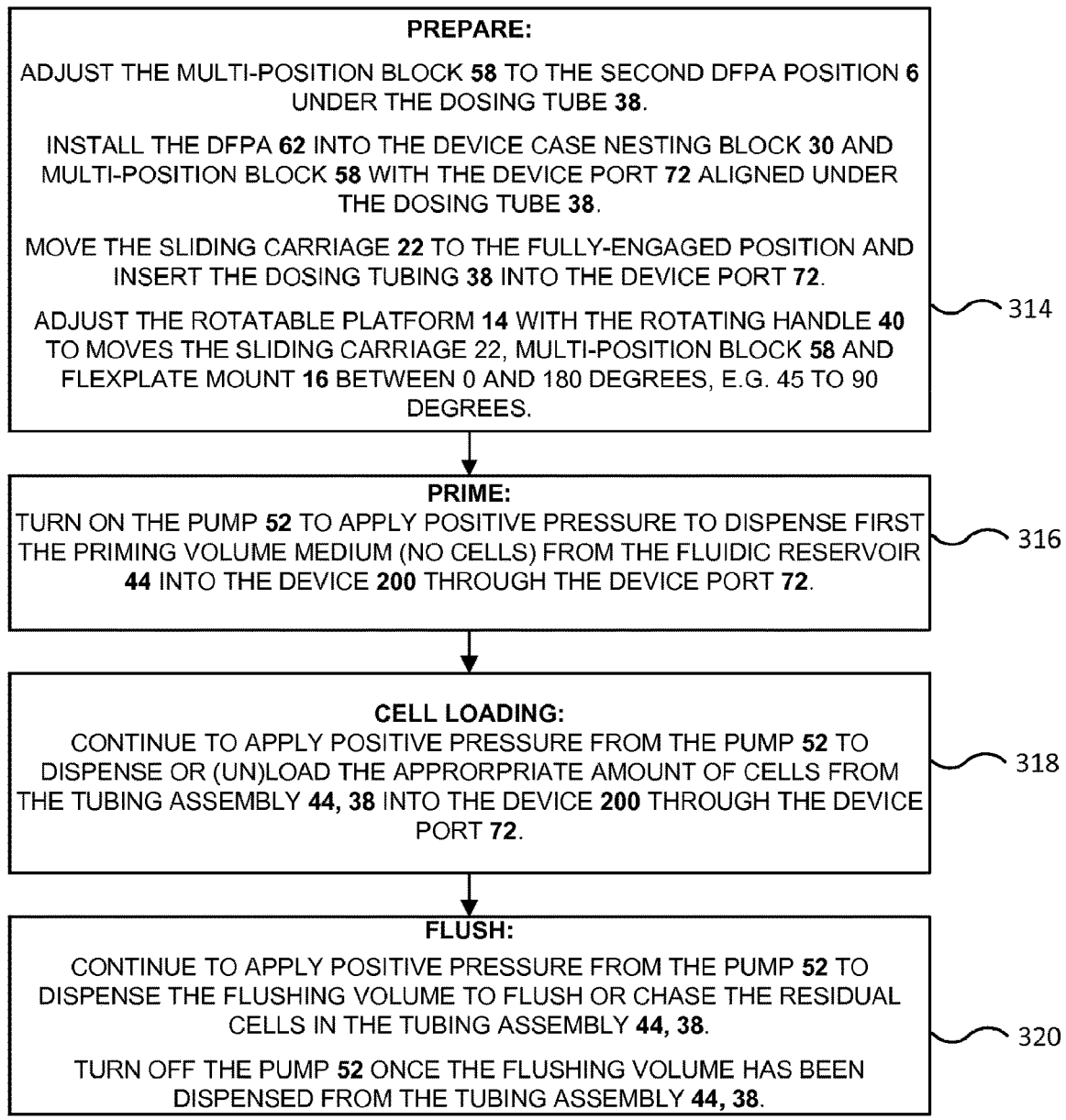
FIG. 10 is a flowchart showing the comprehensive steps for dispensing the tubing assembly with flushing, cells and priming volume into the device, according to an embodiment of the invention.

In one embodiment, when loading the implantable device 200 with cells as further described in FIG. 10, the flexplate mount flexes and maintains a tight connection between the dosing tube and the device port 72 inside the DFPA 62.

Sliding Carriage

The rotatable platform 14 is detachably connected to sliding carriage 22 and moves on a pair of rods 18, capable of engaging and disengaging the dosing tube 38 by movement of the carriage 22 upwards or downwards on the rods 18.

In a preferred embodiment, there are three main activities and volumes: priming with the priming volume, cells in the cell volume, and flushing with the flushing volume. The dose tubing assembly 44, 38, is maintained in place by the flexplate mount 16 as described above. The flexplate mount 16 is detachably connected to the sliding carriage 22 and the sliding carriage 16 is capable of being positioned in three positions relative to the tip of the dosing tube 38. Before the device 200 can be loaded or filled with cells, the dose tubing assembly 44, 38 is first loaded or filled with a flushing volume, a cell aggregate volume, and a priming volume as described in further detail below:

(2) Mid position: The sliding carriage 22 is positioned to a middle position, such that the dosing tube 38 is submerged in the vial medium and suspended above the bottom of the vial 36 (right above the settled cell aggregates). In one embodiment, this middle position can be used to aspirate or pull cell medium or flushing volume only (without aspirating cell aggregates) into the dosing tube assembly 44, 38. Loading the cell media without loading cell aggregates into the dosing tube assembly 44, 38 is desirable because the cell medium has at 2 functions: (i) used to wet (or "prime") the device 200; and (ii) used to flush (or "chase") the cells out of the dose tubing assembly 44, 38 into the device.

(1) Fully engaged: The sliding carriage 22 is positioned most proximally, where it abuts or is in very close proximity to rotatable platform 14 and the flexplate mount 16. If the multi-position block 58 is in the first vial position 4 (FIG. 2A), the dosing tube 38 is then centered over the vial 36 and tip of the dosing tube 38 is near the bottom of the vial 36. If the multi-position block 58 is in the second filling position 6, then the tip of the dosing tube 38 is aligned and inserted into the device port 72 in the DFPA 62. In another embodiment, there can be a fitting in between the device port 72 and the dosing tube 38, e.g., if the dosing tube 38 and device port 72 have different radii. In one embodiment, this fully-engaged position is used to pull the cell aggregates into the dose tubing assembly 44, 38.

(3) Fully disengaged: The sliding carriage 22 is positioned most distally (furthest away from the flexplate mount 16 and the rotatable platform 14) such that the dosing tube 38 is fully disengaged from the device port 72, and/or DFPA 62 or vial 36. In one embodiment, this disengaged position is used to remove or install the DFPA 62 or vial 36.

In one embodiment, any of these 3 positions (mid, fully engaged, fully disengaged) and when to use them will depend on the cells or therapeutic agent in the vial. For example, a preferred embodiment describing loading the dose tubing assembly 44, 38 and loading the device 200 is described herein; however, when the system 1 is used with a therapeutic agent which may be a more homogenous mixture, there may not be separate physical layers. In such an embodiment, separate vials containing cell medium for priming and flushing the therapeutic agent may need to be employed.

Figure 9:
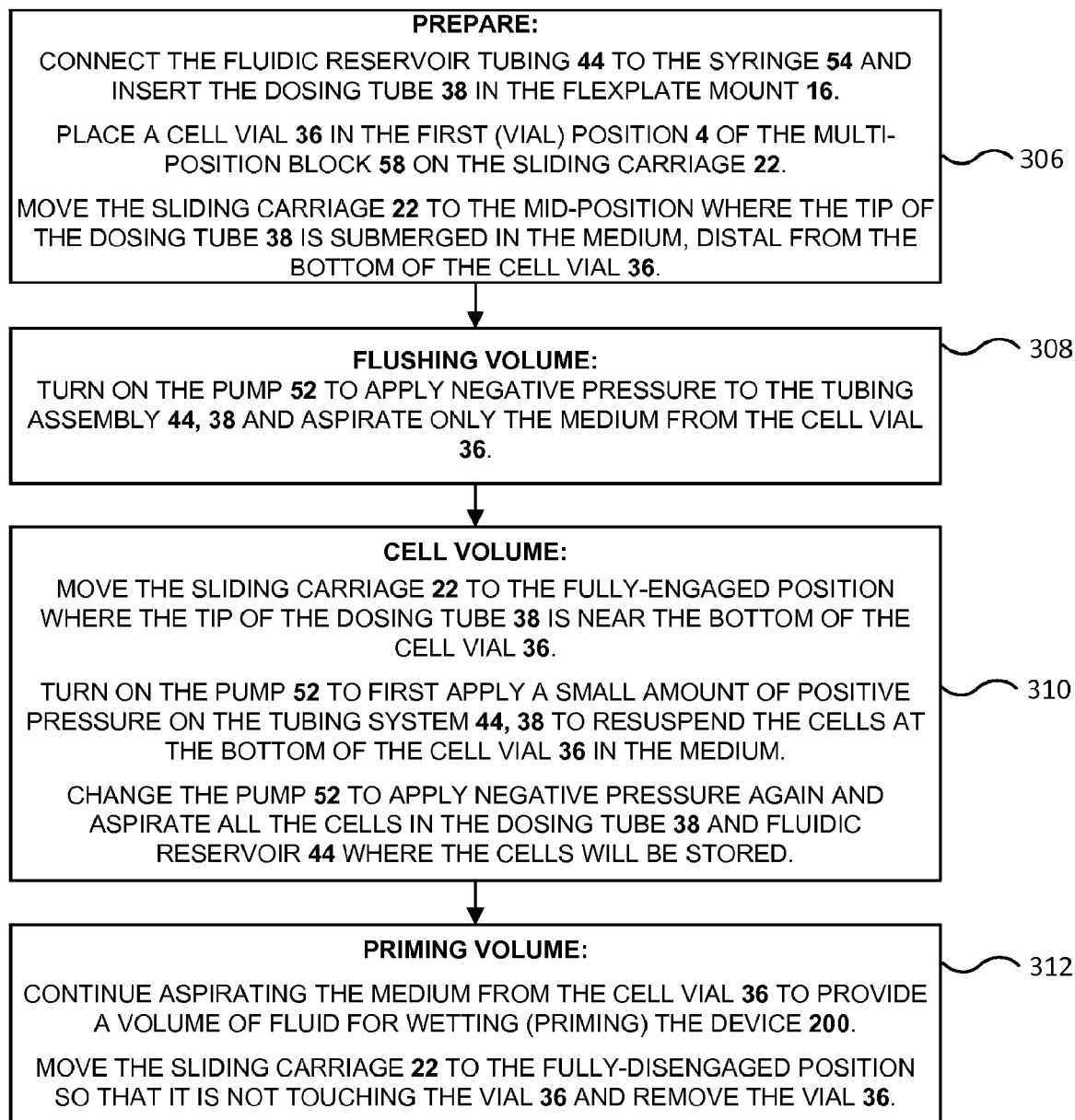
FIG. 9 is a flowchart showing the comprehensive steps for loading the tubing assembly with a flushing, cells and priming volume, according to an embodiment of the invention.

One preferred embodiment of loading the dose tubing assembly 44, 38 and loading the device 200 is described in FIGS. 9-10.

To maintain the sliding carriage 22 in their positions, magnets can be used to retain or lock the position of the carriage 22 at different positions of the travel (the "stop"). In one embodiment, fine tuning or fine adjustment can be accommodated by adding magnetic adjustment screws that can, when moved in either direction, contact the magnet at either end. The stops prevent further movement of the carriage 22 and potential mis-alignment of the dosing tube 38 with either the DFPA 62 or the vial 36. The use of magnets and other stopping methods including other mechanical means can also be used in the adjustable multi-position block 58 as described in more detail below.

In one embodiment, the sliding carriage 22 further consists of an adjustable multi-position block 58 and a DFPA nesting block 30 as described in more detail below.

Adjustable Multi-Position Block

In one embodiment, the sliding carriage 22 further consists of an adjustable multi-position block 58. The adjustable multi-position block 58 is a transverse-sliding platform with at least two (2) positions. FIG. 2 illustrates a first position 4 (the "vial position") whereby a vial 36 can be inserted in the block 58 and a second position 6 (the "filling position") whereby a DFPA 62 can rests, partially or completely, in the multi-position block 58. Thus, the multi-position block 58 can be adjusted depending on the function. In one embodiment, to load the dosing tubing assembly 44, 38 with cells or the desired therapeutic agent, the first vial position 4 is used and can accommodate a cell container or vial 36. In another embodiment, to dispense the cells from the dosing tube assembly 44, 38 into a device (or load the device), the second filling position 6 is used and can accommodate a DFPA or a similar sterile device containing a device 200 with a port. Each of these embodiments is described in more detail below with reference to FIGS. 9-10.

DFPA Nesting Block

In another embodiment, the sliding carriage 22 further comprises a DFPA nesting block 30 and can accommodate any device case and device shape, for example, a device case 74 and device 200 similar to that described in FIG. 2B, held inside the DFPA 62. Hence, the DFPA nesting block 30 can have a recess which accommodates the shape and size of the device case and device.

In one embodiment, the DFPA nesting block 30 also holds the device case 74 and device 200 upright for sealing the device port 72, as described in more detail below.

Over-Center ("Toggle") Clamps

In one embodiment, the adjustable multi-position block 58 and the DFPA nesting block 30 further consist of over-center clamps (or toggle clamps)28, 32 to secure a vial 36, or DFPA 62, in place. In one embodiment, the toggle clamps 28, 32 can be in the form of elongated contact bars that move into position to retain and hold the aliquot vial 36 and/or the DFPA 62 during operation. In one embodiment, the clamps (or contact bars in this instance) 28, 32 are connected to the clamp levers 24, 26, which are operated to open and release the clamps to hold the vial 36 or the DFPA 62. As with other embodiments, a method for securing or holding a vial 36 or DFPA 62 in place can be accomplished with any number of applications capable of opening and closing a clamp-like grip or holder. The clamps 28, 32 can be made of a flexible material such that the fingers on the clamps can accommodate variations in vial 36 size or DFPA 62 thickness, so that the priming and loading system 1 can be used and optimized for various devices. And, at least for the adjustable multi-position block 58, any clamp 32 should allow the adjustable multi-position block 58 to slide between its two positions with the clamps 28, 32 fully depressed. Other retention mechanisms are also possible including but not limited to latches, snaps, locking female and male parts, tabs and the like.

The embodiments of the priming and cell loading system 1 therefore provide features with multiple adjustable components to accommodate different functions and applications. Because the adjustable multi-position block 58 slides from a first vial 4 position for aspirating the cells into the dosing tube assembly 38, 44 with the flushing, cell and priming volumes 4, and to a second filling 6 position for dispensing the priming, cell and flushing volumes. Further, after loading the device 200, the device port 72 can be easily sealed while the device 200 is still inside the device case 74 and inside the DFPA 62. These multiple function also reduces risk of contamination because operations are performed in one area. The various system 1 components also provide for user optimization based on the device being used.

Device Port Sealer

Figure 4A:
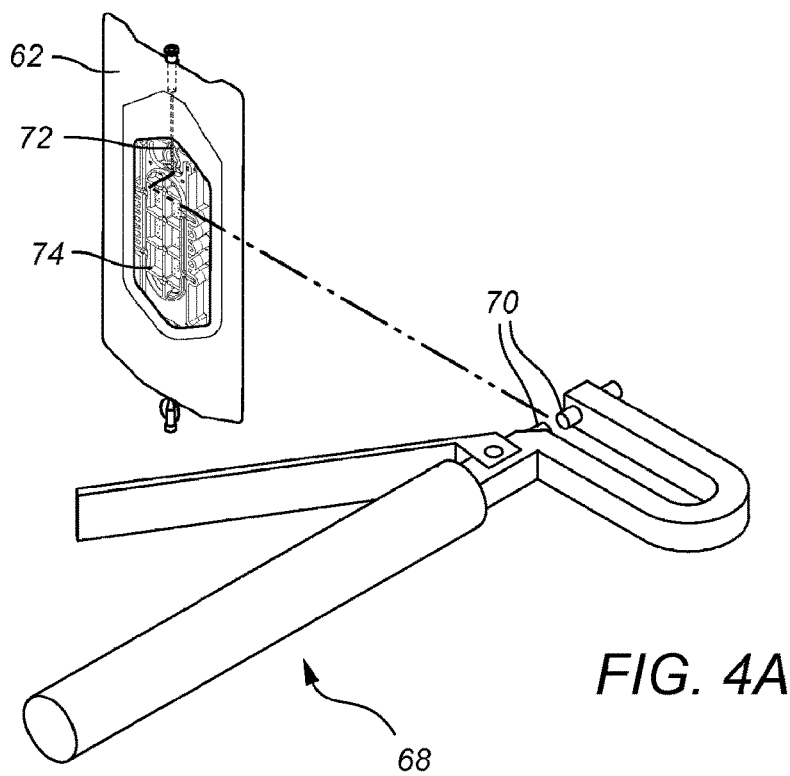
FIGS. 4A & B illustrate a perspective view of a hand-held radio frequency (RF) sealer in a retracted position (A), and in an engaged position (B) sealing the device port, according to an embodiment of the invention.
Figure 4B:
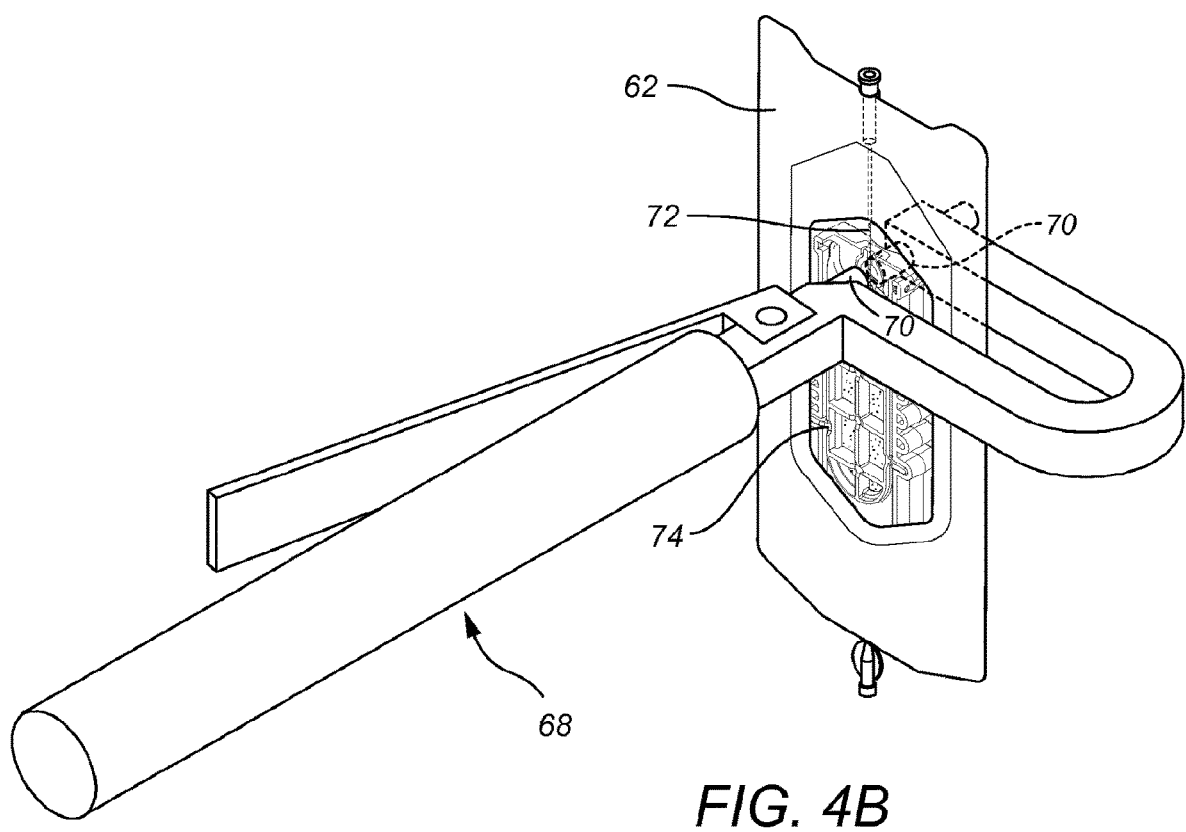

Once the implantable device is primed (wetted), loaded with cells, and the cells flushed from the dosing tube, the device needs to be sealed to prevent escape of the therapeutic cells and/or agents loaded therein. FIG. 4 illustrates a nonlimiting, nonexclusive embodiment of such a device port sealer 68.

In general, the device port sealer 68 comprises at least four parts: an RF generator, a transmission cable, a sealing wand with internal matching network, and a custom set of sealer electrodes 70 configured such that the electrodes are located at the end of C-shaped jaws. This C-shaped configuration allows for access to the device port 72. In a preferred embodiment, the C-shaped jaws wrap around the sealing port area of the device case 74 to seal the device port 72 without breaching the DFPA 62. The C-shaped also allows the jaws to slide over the DFPA 62 from either side and permits direct access for the electrodes to about the center of the DFPA 62 where the device port 72 would typically reside. The sealer electrodes 70 are cylindrical in shape and mate with corresponding cylindrical cutout sections in the device case 74. The electrode position is adjustable within the jaws, to permit a fixed electrode gap to be present when the sealer wand handle is completely closed. The sealer electrodes 70 in the jaws can be quickly replaced should they become soiled, damaged or pitted due to RF arcing. Other electrode shapes and configurations are feasible.

In one embodiment, radio frequency (RF) power from a hand-held device port sealer 68 is used to seal the device loading port 72 aseptically (i.e. the device loading port 72 is sealed while still inside the device case 74 and DFPA 62).

In a preferred embodiment, the device 200 is sealed while still in the DFPA nesting block 30 but not necessarily in the second filling position 6 on the adjustable multi-position block 58 so long as the device 200 is maintained in a position so as to prevent accidental leakage or creeping of cells out of the device 200.

In one embodiment, the device loading port 72 is made of any biocompatible flexible plastic tubing that responds particularly or selectively to RF energy and internally heats and cools rapidly while the other materials for the DFPA 62 and device case 74 do not respond similarly to RF energy. For example, using a modest amount of pressure, the heated device loading port 72 can be compressed shut to create a permanent seal in the tubing without the introduction of any additional sealing material (e.g. no sealant, or adhesive film) nor damaging the device loading port 72; while at the same time leaving the case 74 and DFPA 62 unaffected (not sealed e.g. DPFA sheets do not melt together) by the RF sealer. In this instance, the DFPA material acts as a buffer material. Other buffer materials are described below. This ability to permanently seal the device tube aseptically after the device has been filled is unique to this system.

In one embodiment the device port 72 extends beyond the device case 74 as shown in FIG. 4, or extends as necessary to accommodate connecting with the dosing tube 38, and the device port capable of being sealed in any of these regions, although it is usually sealed in the region closest to the body of the device 200 itself.

Thus, during the priming and loading of the implantable device 200, the device 200 is never touched with human hands and is minimally manipulated, and any and all manipulations are within the confines of an aseptic environment of the DFPA 62.

Buffer Material not Reactive to RF Energy

In one embodiment, the buffer material used to make the DFPA or other sterilization bags and pouches was utilized. The DFPA consists of a thin laminate of polyester (e.g., Mylar) and polyethylene, nominally about 0.0025" inches (or 0.0065 mm, or approximately 0.01 mm) thick. This material provides a protective surface between the device port 72 and the sealer electrodes 70, such that the electrodes never directly touch the device loading port while still capable of sealing it. During sealing, the device port 72 reacts to the applied RF energy and heats while the buffer material laminate of the DFPA 62 for example does not. So, under modest clamping pressure, the heated device loading port 72 forms a permanent seal, while at the same time the cooler buffer material laminate does not stick or adhere to the heated loading port. Upon release of pressure after sealing, the sealed port is freed from the buffer material laminate.

In another embodiment, any material or laminate of materials which does not respond to RF energy can be used as a buffer material. The actual thickness of the buffer material is not critical, although thinner materials are preferred for ease of use and lower cost. Alternate materials include polyethylene (e.g. Tyvek), polytetrafluoroethylene, polypropylene, polyamide, etc. A polyester/polyethylene laminate was selected as it is readily available at low cost in thin, easy-to-use sheets. A buffer material that is also transparent, e.g., Mylar polyester, allows the operator to quickly visually inspect the resultant seal aseptically without having to open the DFPA 62.

Still, other materials for the buffer material are described in PCT/US2014/034425, TOOLS AND INSTRUMENTS FOR USE WITH IMPLANTABLE ENCAPSULATION DEVICES, filed Apr. 16, 2014; U.S. application Ser. No. 14/254,844, TOOLS AND INSTRUMENTS FOR USE WITH IMPLANTABLE ENCAPSULATION DEVICES, filed Apr. 16, 2014; and 29/488,209 CASE FOR AN ENCAPSULATION DEVICE, filed Apr. 16, 2014.

Radio Frequency (RF) Generator

In one embodiment, a RF generator utilized to seal the device port 72 comprises self-regulated power output until one of two output conditions is met: (i) Power is delivered until a total energy threshold is achieved, or (ii) Power is delivered until a certain period of time (e.g. 2 seconds) has elapsed. Due to the design of the RF generator and the fixed matching network in the sealing wand, the actual power output fluctuates during the completion of the seal. Nominal power output is approximately 25 W. U.S. Pat. No. 5,349,166 describes in detail the power generation and delivery of RF energy for tubing sealing applications.

In one embodiment, a "Haemonetics" (formerly known as "Sebra") model 2600 RF generator was used to provide RF power to seal the implantable device loading port 72. The generator outputs RF power at an FCC-mandated frequency of 40.68 MHz, via an industry standard 50-Ohm BNC connector. In another embodiment, other frequencies of 13.56 MHz, 27.12 MHz, and 40.68 MHz may also be applied. The model R601 RF generator has a maximum power output of 600 W and can be driven in pulsed or continuous mode. Alternate RF generators can be used but may require additional controls in order to deliver the appropriate power for the specific duration necessary to properly seal the device loading tube. RF generators with such features are available from other manufacturers including but not limited to Seren IPS, Comdel, Lesker, MKS Instruments, and the like.

RF Cable

In one embodiment, a double-shielded, industry standard 50-Ohm impedance RG-223 RF cable is used to transmit the RF energy from the RF generator to the sealing wand. The length of this cable is about 95.8", and is specifically tuned to be ½ wavelength at 40.68 MHz. This length maximizes transmission efficiency and minimizes back reflections between the RF generator and the sealing wand.

In another embodiment, other 50-Ohm RF cables can also be used (RG-6, RG-58, RG-174, etc.) but vary in stiffness, shielding (decreased efficiency), or current capacity.

In one embodiment, a "Haemonetics" (formerly known as "Sebra") sealing wand is used to provide RF impedance matching between the RF source and the load, as well as ergonomic access for the user to bring the sealing jaws into position around the DFPA 62. Due to the unique shape and configuration of the device loading port sealer 68 jaws, the sealer head load impedance differs from the industry standard 50-Ohm resistive impedance. To correct for this variation, an intermediate corrective inductive/capacitive impedance (matching network) is placed between the RF source and the load. The sealing wand features an internal matching network consisting of fixed value capacitor(s) and inductor(s). The sealing wand matching network is manually tuned at the factory and results in a lightweight, compact, efficient matching network. U.S. Pat. No. 4,013,860 (incorporated by reference in its entirety) describes in detail the fixed value matching network located inside the sealing wand.

In another embodiment, a tunable matching network can also be used, but with additional cost and space consumption. Other tunable matching networks are available from select manufacturers including but not limited to Seren IPS, TC Power Conversion, Manitousys, Materials Science Inc., and the like. Use of the Haemonetics Model 1105 sealing wand with fixed matching network results in a lower cost, more compact sealing solution.

Device Case Storage Bag Sealing Station

Figure 5:
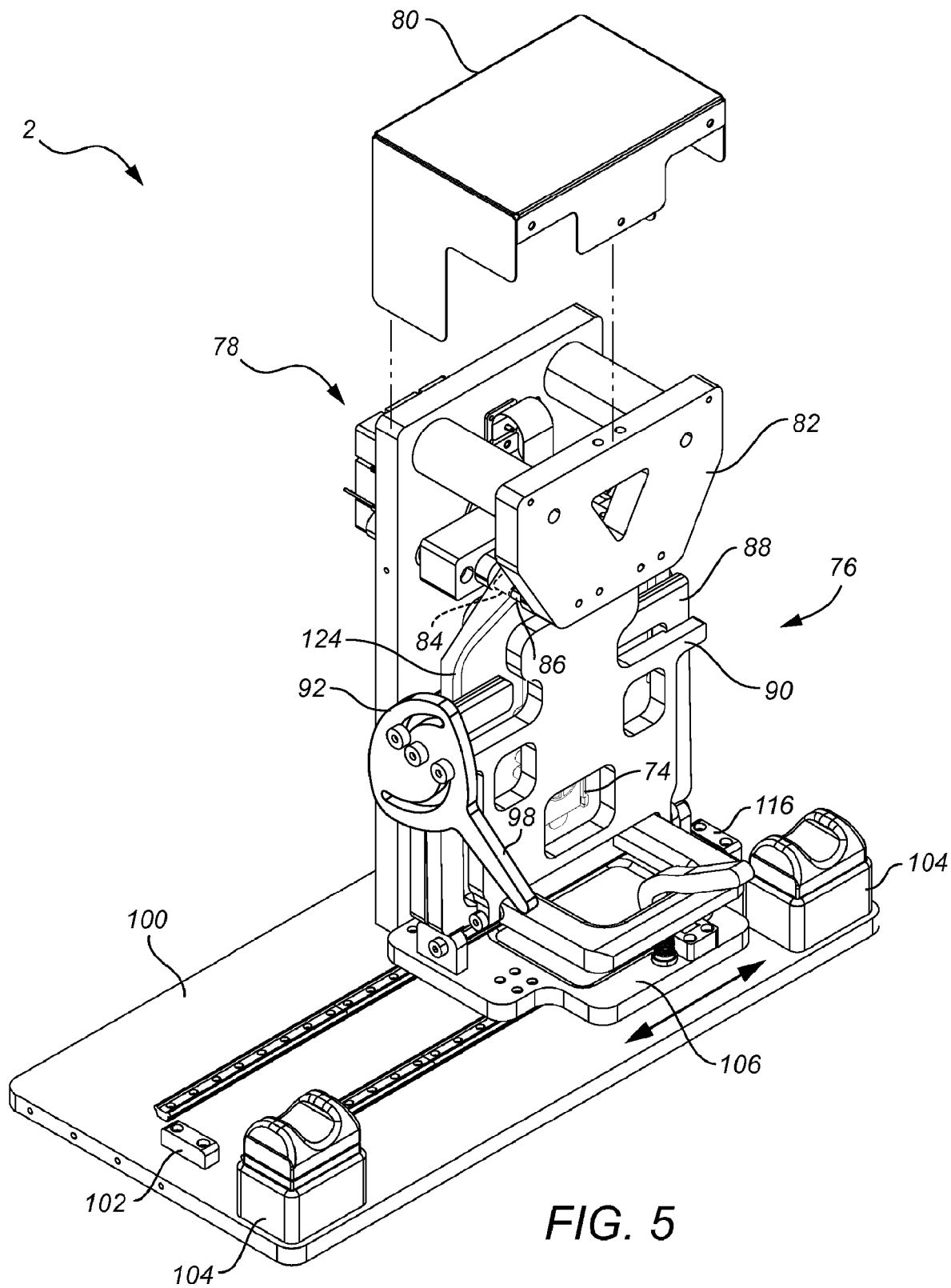
FIG. 5 illustrates a perspective view of a device case storage bag sealer consisting of a device case storage bag holder with a pair of first holder plates and a pair of second swinging plates for holding the device case storage bag having an RF-reactive or sensitive portion, an adjustable opening and closing system for each of the pair of first and second plates, wherein the holder rests on a sliding carriage capable of moving the holder from the loading position under the sealing head assembly to seal the device case storage bag.
Figure 6A:
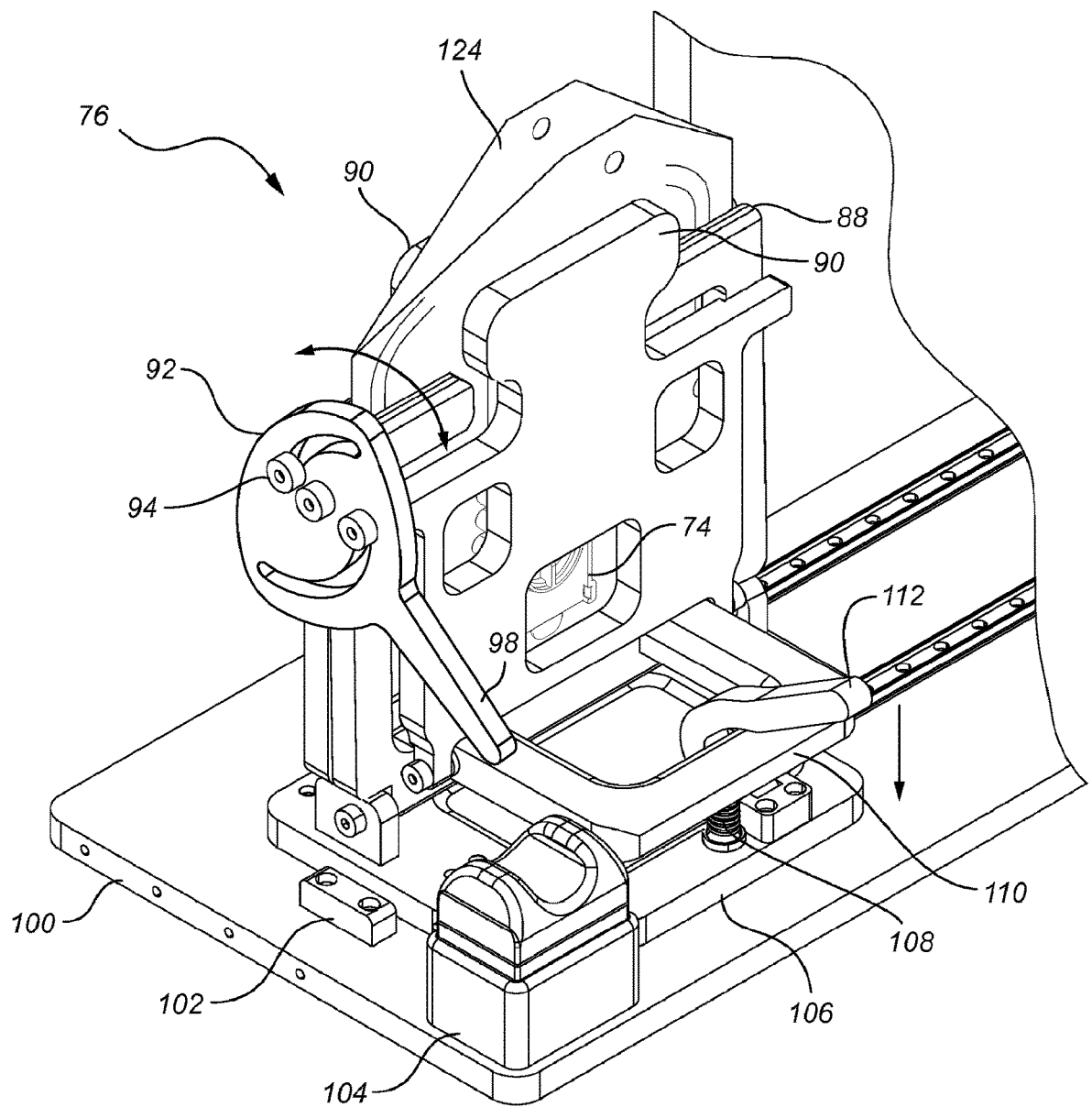
FIGS. 6A &B illustrate a larger perspective view of a device case storage bag holder with an open and unsealed device case storage bag (A) resting on a sliding carriage and adjustable opening and closing systems for the holder; and (B) wherein the device case storage bag is closed and sealed according to an embodiment of the invention.
Figure 6B:
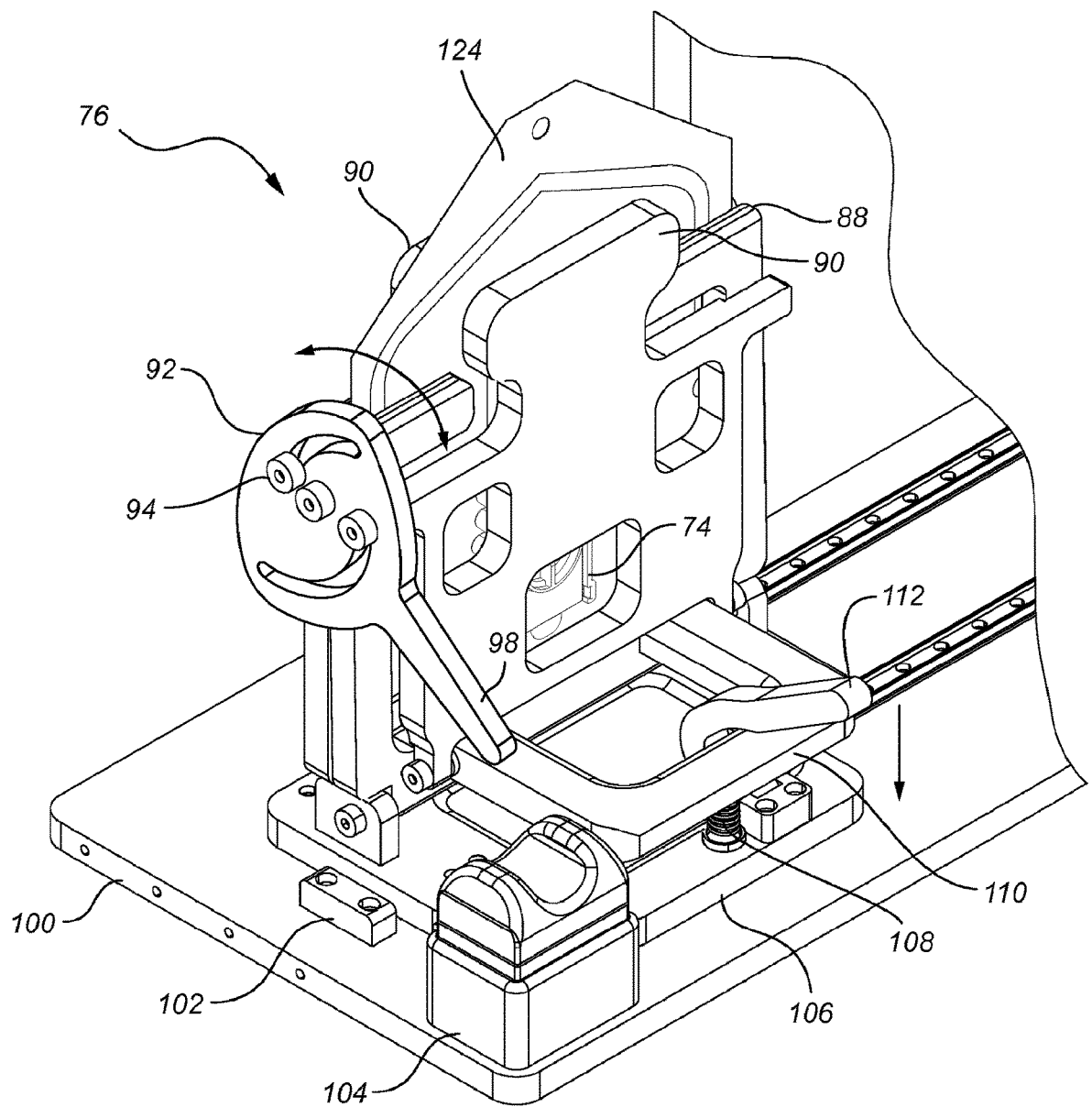
Figure 7:
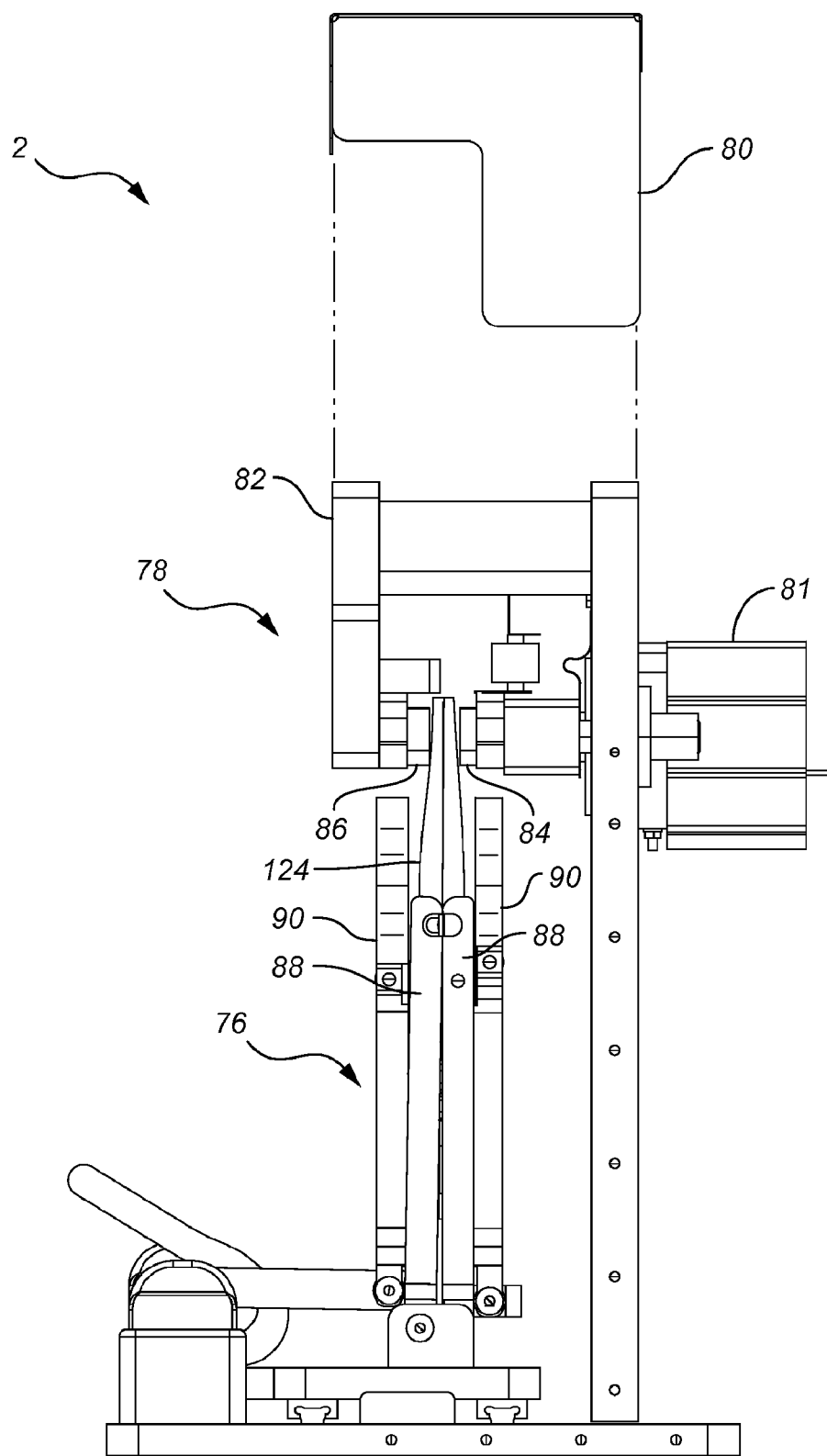
FIG. 7 illustrates a side view of a device case storage bag holder under the sealing head assembly, according to an embodiment of the invention.

FIGS. 5-7 illustrate nonlimiting, nonexclusive embodiments of a device case storage bag sealing station 2 for sealing or closing a device case storage bag 124, which further consists of a loaded implantable device 200 inside a device case 74.

In general, the sealing station 2 consists of at least a device case storage bag holder 76 and a sealing head assembly 78 on a base 100.

Device Case Storage Bag

FIGS. 6A-B illustrates nonlimiting, nonexclusive embodiments of a means for storing a cell-filled or cell-loaded device (or cell encapsulated device) in a storage bag 124.

The configuration of the device case storage bag 124 was designed hand-in-hand with the sealing station 2. Features on the sealing station 2 for example directly interface with the device case storage bag 124 and was based on at least 2 basic requirements: (i) to protect the device and therapeutic cells or agents inside the device during shipping and handling, and (ii) to allow for a final seal to be applied aseptically. A detailed description of this and similar storage bags are described in Applicants PCT/US2014/034425, TOOLS AND INSTRUMENTS FOR USE WITH IMPLANTABLE ENCAPSULATION DEVICES, filed Apr. 16, 2014; U.S. application Ser. No. 14/254,844, TOOLS AND INSTRUMENTS FOR USE WITH IMPLANTABLE ENCAPSULATION DEVICES, filed Apr. 16, 2014.

In one embodiment, certain features such as holes or cut-outs can be incorporated into the device case storage bag 124 during design and manufacture that align with corresponding features or markings (e.g. ink markings) on the first holder plates 88. This is analogous to male and female parts of a latch or fitting. Hence, any sealing station 2 may incorporate features of the item being sealed or have corresponding features from the item being sealed (e.g. alignment features on the device case storage bag 124 and the sealing station 2).

Device Case Storage Bag Holder

In one embodiment, the device case storage bag holder 76 sits on a sliding carriage 106 and consists of first holder plates 88 and second swinging plates 90. In one embodiment, the 2 plats making up the holder plates 88, do not move or pivot equally, e.g., the front plate may pivot while the back plate is stationary. The first holder plates 88 hold the device storage bag 124 and is controlled by a cam or lever 112 further connected to bar or plate 110, and the plate 110 is connected to a spring 108 and capable of moving (or pivoting) the lever 112 pivots a bar/plate 110. For example, to lock the device case storage bag to the first holder plates 88, the lever 112 is pulled upward, which is mechanically translated to the front plate 88, pinching the device case storage bag holder 124 into the holder 76; and to release the device case storage bag 124, the lever 112 is pushed downward.

The device case storage bag holder 76 holds the device case storage bag 124, with the device case 74 and the cell-loaded device 200. In one embodiment before sealing the device case storage bag 124, the cell-loaded device 200 inside the device case 74 is removed and transferred from the DFPA 62 to the opened and unsealed bag 124. The first holder plates 88 are primarily responsible for keeping the storage bag 124 in place and open while the storage bag 124 is being filled, i.e. while the device case 74 and device 200 are being transferred into the storage bag 124 and while the storage bag 124 is being filled sufficiently to bathe or cover the device case 74 and device 200 with a liquid medium for long-term storage i.e., a storage buffer.

In another embodiment, the second swinging plates 90 are responsible for closing the now device and medium-filled unsealed device case storage bag 124. The opening and closing of the second swinging plates 90 is controlled by the cam 92 and cam lever 98 that moves about the cam guides.

In one embodiment before sealing the device case storage bag 124, residual or excess air in the bag 124 needs to be removed so that there is the least amount of air in the bag 124 as possible after sealing. To remove the residual air in the bag 124, the cam lever 98 which is rotatable along the cam guides is moved to a closed position whereby it compresses the device case storage bag 124 residing in between the first holder plates 88. This action pushes and removes residual air from the device case storage bag 124 up and out of the bag 124 such that the storage medium for example is near the top of the bag 124 prior to sealing. Sealing of the device case storage bag 124 is described in more detail below.

Device Case Storage Bag Sliding Carriage

The device case storage bag holder 76 can rest on a sliding carriage 106, which is capable of moving the holder 76 horizontally (left and right), and in particular, under the sealing head 78 of the sealing station 2.

In one embodiment, the sliding carriage 106 slides back and forth by resting or sitting on any number of rails, or grooves. In another embodiment, the rails have stops 102, 116 at each end to prevent the sliding carriage 106 from traveling further or sliding off. For example, in one embodiment, the sliding carriage 106 sits on 2 rails and the stops 102, 116 are attached or located on the base 100, however, any number of rails can work and the stops 102, 116 can be located in any location whereby they prevent further movement of the sliding carriage 106.

Together, the sliding carriage 106 along with the device case storage bag holder 76 provides an aseptic working environment to capture an open (unsealed) device case storage bag 124 for receiving the device case 74 and the loaded implantable device therein and sealing such in the storage bag using the sealer described herein.

Sealing Head Assembly

In one embodiment the sealing station 2 consists of a sealing head assembly 78 protected by a shield 80, with mounted horizontally opposed RF electrodes 84, 86. The rear electrode 84 is mounted on an air cylinder 81 and the front electrode 86 is fixed. To seal the device case storage bag 124, the sliding carriage 106 moves the entire holder 76 under the sealing head assembly 78.

To seal the storage bag 124, a nominal gap provides for insertion of the device case storage bag 124 in between the electrodes 84, 86 (thereby separating the two electrodes), and the air cylinder 81 is extended and the rear electrode 84 travels forward to enclose the device case bag 124 between the two electrodes 84, 86 and application of RF power heats the RF-reactive portion of the bag 124 and forms the seal on the bag 124 (FIG. 6B). Retracting the air cylinder 81 unclamps the device case storage bag 124 from the electrodes 84, 86, and the sliding carriage 106 can be returned to a position away from under the sealing head assembly 78 (moved to the left as illustrated).

Automation of the RF Sealer

Operations for sealing the device case storage bag 124 can be fully or semi-automated. In one embodiment, a personal computer (PC) is used to communicate with the RF generator (e.g. a Seren RF Generator) and matching network (e.g. the Seren Matching Network) to perform the sealing operations. Both the RF generator and matching network are fully-configurable for various user applications but require, for at least in the example of the Seren RF generator and matching network, specific operating commands from an external controller (i.e. they are not enabled with programmed software to perform the operations discussed above).

Still in other embodiments, other control schemes are possible. For example, a programmable logic controller (PLC) can maintain the various Seren initialization and RF generation command strings, and then send these commands to the Seren RF generator upon user demand. The Seren matching network normally does not require any periodic commands to be issued after its initial configuration has been empirically determined and internally configured. In one embodiment, a PC for the control scheme is used.

In another embodiment, a simple activation switch 104 can be used to control the sealing station 2.

RF Generator

In one embodiment, an off-the-shelf Seren Industrial Power Supplies R601 Radio Frequency Generator was utilized for precision application of RF power to achieve heating and sealing of the RF-responsive EVA layer of the device case storage bag 124. The FCC mandates frequencies of 13.56 MHz, 27.12 MHz, and 40.68 MHz for these types of applications, and in one embodiment, 40.68 MHz was selected. The model R601 RF generator has a maximum power output of 600 W and can be driven in pulsed or continuous mode. Its RF output is via industry standard N connector and industry standard 50-Ohm impedance transmission cables. RF generators with similar features are available from other manufacturers (e.g., Comdel, Lesker, MKS Instruments, etc.). Seren was selected for providing a rich feature set and serial command capability.

Matching Network

Due to the unique shape and configuration of the final seal on the device case storage bag 124, the sealer head load impedance differed greatly from the industry standard 50-Ohm resistive impedance. To correct for this variation, intermediate corrective inductive/capacitive impedance is placed between the RF source and the load. A Seren ATS-10M Matching Network achieves this intermediate correction and provides simple operator tuning adjustments available via RS-232 serial communications.

In another embodiment, a matching network can be constructed manually, with fixed inductor(s) and capacitor(s) as appropriate. This technique has a lower final cost, but with a high labor cost because it is very time intensive to empirically test variations in both inductance and capacitance simultaneously to achieve matched impedance.

Other tunable matching networks are available from select manufacturers (e.g., TC Power Conversion, Manitousys, Materials Science Inc., etc.). Seren was selected in order to assure vendor compatibility between the RF generator and the matching network.

Crimping Sealer

In an alternative embodiment, the flexible nature of the device port 72 may be sealed using a crimpable band or ring around the device port 72. The crimpable band or ring may consist of a metal or metal material or a high strength polymer material. In one embodiment, the metal or polymer material is stronger than the material from which the device port is formed.

In another embodiment, the ring or band is configured to snap-fit around the device port 72.

Similar in concept to the hand-held tool described in FIG. 4, in one embodiment, the sealing is accomplished by means of a crimping tool. Examples of crimping tools have been described including but not limited to U.S. Pat. Nos. 7,226,425, 8,376,741, 5,267,464, which are incorporated herein in their entireties. Such a crimping tool may also provide a mechanism for controlling the location of the crimp, by providing a stop that allows consistent placement of the crimped section on the device port (e.g. the region closest to the device 200).

Shipping Bag Sealer

Figure 8:
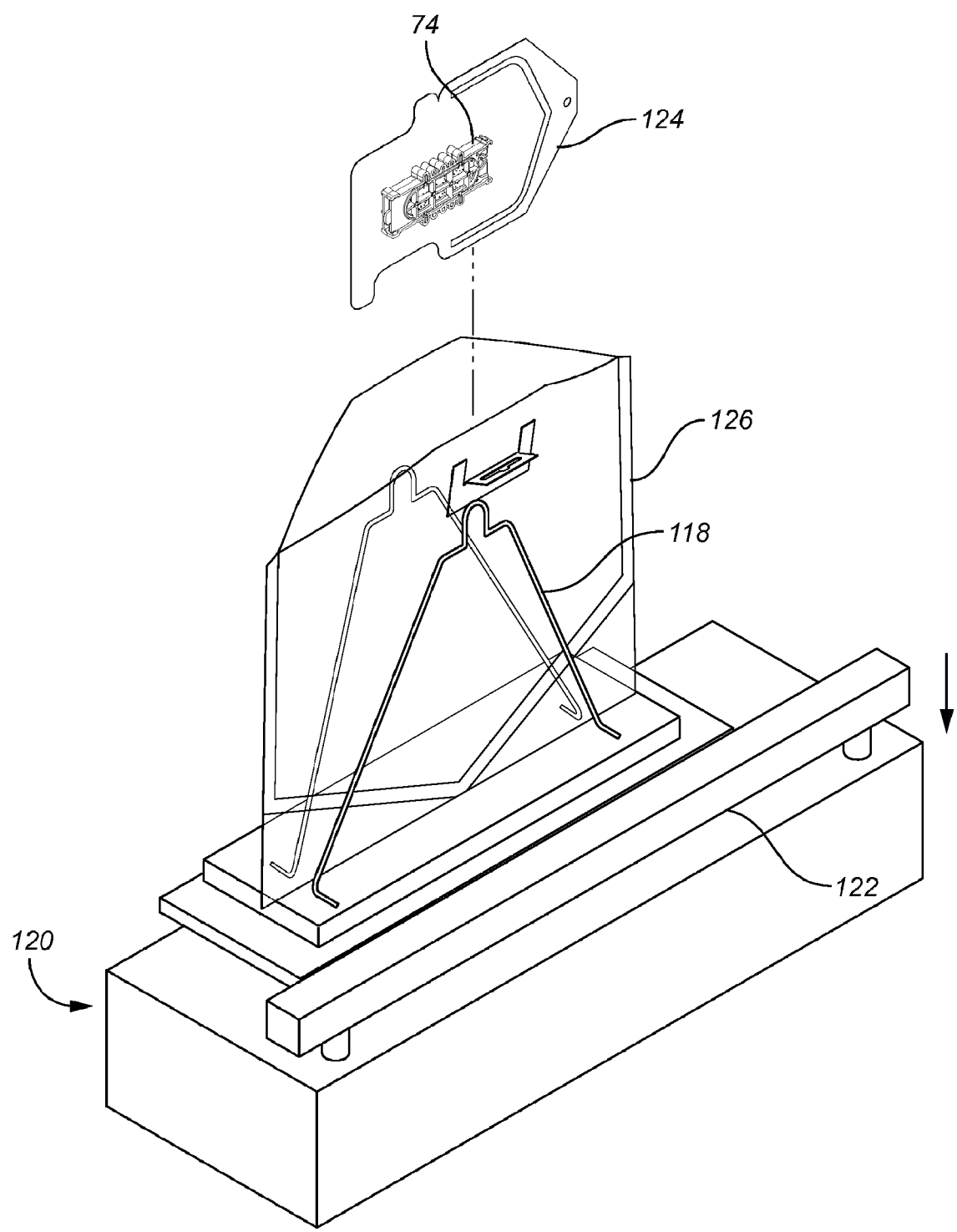
FIG. 8 illustrates a perspective view of a shipping bag for housing a device case storage bag and a sealer for sealing the shipping bag, according to an embodiment of the invention.

FIG. 8 illustrates a nonlimiting, nonexclusive embodiment of a sealing system 120 for sealing or closing a shipping bag 126 containing for example a device case storage bag 124, device case 74, and a device therein.

In one embodiment, the sealer is a temperature controlled, pneumatic impulse heat sealer designed for use in heat sealing pouches or bags generally. In one embodiment, the heat sealer is an Impulse Sealer from Accu-Seal (e.g. Model 5300-5400 Series). Heat sealers may be controlled by digital, high speed, programmable logic controller (PLC) with compatible screens. The settable parameters include temperature, sealing time (or dwell), seal release temperature and seal pressure. These and other heat sealers are portable and can be operated on almost any tabletop or stand. The heat sealer has a heating element, which can be detachably connected under the touchable sealer bar 122. The shipping package or bag 126 is sealed by placing the bag opening under the heating element, or under the touchable sealer pressure bar 122, and then run the sealing parameters (heat temperature, dwell, pressure, etc.). In this model, once the sealing parameters have been performed the seal bar will open allowing the removal of the shipping package 126.

FIG. 8 also illustrates a holder 118 for holding or positioning the shipping bag 126 in preparation of aseptically receiving the sealed device case storage bag 124. The holder 118 can be made of any appropriate metal or wire and is mounted on a portable base, which can be moved anywhere convenient for the operator and the function to be performed.

Methods for Priming, Cell Loading and Sealing of Devices and Associated Storage and Shipping Bags FIGS. 9-11 illustrate non-limiting, non-exclusive methods and means for priming, cell loading, flushing and sealing of devices and storage and associated storage and shipping bags therewith.

FIG. 9 describes embodiments and/or operations for preparing 306 for loading the tubing assembly with a flushing 308, cell 310 and priming volume using the cell loading system 1. In an operation 306 to prepare and set up the system 1 by first loading the dose tubing assembly 44, 38. The dose tubing assembly 44, 38 is pre-connected to the syringe 54 and the two are sterilized together and then further connected to the syringe pump 52. In an operation 308, the pump 52 is turned on and a negative pressure or positive pressure can be applied to pull (or load, or aspirate) and dispense (or load) the different fluid volumes into the dose tubing assembly 44, 38 and out the dose tubing assembly 44, 38, respectively. In another operation 310, the fluid volumes are loaded into the dose tubing assembly 44, 38 in the reverse order that the volumes will be dispensed. For example, when loading cells into the device 200, the device 200 is first primed or wetted (priming volume), then loaded with cells (cell volume or cell aggregate volume) and finally the cells are flushed or chased (flushing or chasing volume) out of the dose tubing assembly 44, 38. This order is reversed in operations 308, 310 and 312 of FIG. 9 whereby the same volumes are loaded in reverse into the dose tubing assembly 44, 38. So, the dose tubing assembly 44, 38 is first loaded with operation 308, the flushing volume, operation 310, the cell aggregate volume, and then operation 312, the priming volume.

In another preferred embodiment, the cell vial 36 containing the cell aggregates provides all 3 volumes: flushing volume, cell aggregate volume and priming volume. The sliding carriage 22 is adjusted vertically (y-axis) as described above (mid-position, engaged, disengaged) such that the tip of the dosing tube 38 aspirates certain of these volumes from the aliquot or cell vial 36 specifically when the multi-position block 58 is in the first vial position 4. If all 3 volumes can be loaded from one vial, the tip can be adjusted to aspirate the flushing volume at mid-position; and aspirate the cell aggregate volume and priming volume at the fully-engaged position. However, if the 3 volumes, or additional volumes (e.g. wash volume, additional priming or wetting volume, additional cells, additional therapeutic agent and the like), cannot be loaded form a single vial, then multiple vials containing the specific volumes can be inserted accordingly.

FIG. 10 describe embodiments and/or operations for dispensing into the device 200 from the dose tubing assembly 44, 38 the priming volume 316, cell volume 318, and flushing volume 320 using the cell loading system 1. In an operation 314, the system 1 is prepared by moving the multi-position block 58 into the second filling position 6 and the sliding carriage 22 is moved to a fully-disengaged position such as to insert the distal part of the DFPA 62 into the DFPA nesting block 30 and the proximal part of the DFPA 62 is inserted into second filling position 6. The sliding carriage 22 is then moved to a fully engaged position and the dosing tube 38 is connected to the device port and the rotatable platform is positioned between 45 to 90 degrees relative to the base 34. To load cells into the device, in operations 316, 318, 320, the pump is turned on and positive pressure is applied to dispense the priming (or wetting) volume 316 to wet the device 200, the cell aggregate volume 318, and then the flushing volume 320 to chase or flush the cells (e.g. those remaining in the dose tubing assembly 44, 38).

It will be apparent to one skilled in the art that these volumes can be repeated if there are multiple devices to be filled, or fewer or additional volumes can be aspirated and dispensed from the dosing tube assembly 44, 38 depending on the function and type of device, as well as each individual volume to be aspirated into the dose tubing assembly 44, 38 to be supplied by different vials or cell, therapeutic agent or medium sources. In one embodiment, operations for priming volume, cell volume and flushing volume, can be repeated 2, 3, 4, 5, 6, 7, 8 or more times with the same vial or reservoir into the dosing tube assembly 44, 38 if desired and so long as there is sufficient tube length. In another embodiment, the more than 1, 2, 3, 4, 5, 6, 7, 8 or more volumes can be aspirated into the dose tubing assembly 44, 38 from different vials or reservoirs.

FIG. 11 describes steps and/or operations for sealing a device 322, steps for storing and sealing a device case storage bag 324 and steps for sealing a shipping bag 326, at least a shipping bag containing a device case storage bag, device case and cell-loaded device.

In an operation 322, cells leaking from the device 200 are prevented by sealing the device port 72 immediately or promptly after the loading the device 200 as described above. With the DFPA still in the DFPA nesting block 30, the C-shape jaws of the hand-held RF sealer 68 is placed around the DFPA near the device port 72 area or near the device port sealing area of the device case 74. Closing the sealer handle provides a sufficient amount of pressure on the electrodes 70 on the device port 72 and initiates RF energy thereby sealing the device port 72. Importantly, the RF electrodes do not seal the sheets of the DFPA 62 together nor do the seal the DFPA 62 to the device port 72. As discussed above, there are other materials which selectively react to RF energy while other materials are un-reactive to RF energy. The advantage of an RF energy reactive and un-reactive material for the DFPA 62 or any bag or container (made of a one material) for the device 200 is that it allows for the device port 72 (made of second material) to be sealed aseptically while still in the DFPA 62.

After the device is loaded with cells and the device port 72 is sealed, the cell-filled or loaded device is ready to be stored and shipped to the implantation or surgical site for implantation. FIG. 10 describes an operation 326 for storing the cell-loaded device in a device case storage bag 124 using a device case storage bag sealing station 2. To prepare for the device case 74 and cell-filled device, the device case storage bag 124 is placed and aligned between first holder plates 88 of the device case storage bag holder 76 and closed by pulling up on the clamp lever 112. The device case 74 and cell-filled device are then carefully removed from the DFPA 62 (e.g. removed by way of the frangible, removable see-through window on the front or one side of the DFPA) and any excess device port 72 is removed. The device case 74 and cell-filled device are then placed into the device case storage bag 124 and the bag filled with a liquid storage medium. Sufficient medium is used to submerge both the device case 74 and cell-filled device. To remove or expel residual air from the device case bag 124, the second swinging plates 90 are closed using the cam lever 98. The swinging 90 and holder 88 plates can be made to operate independently of each other or coupled. In one embodiment, the plates 90, 88 are coupled and closing the swinging plates 90 will also close the first holder plates 88 and put pressure on the device case storage bag 124 pushing any residual air up to the top of the opened and un-sealed bag 124. In another embodiment, the plates 90, 88 are not coupled or independent, and closure of one does not close the other.

The device case storage bag holder 76 rests on a sliding carriage 106, which can then move the holder 76 under the sealing head assembly 78 to seal the opened and un-sealed storage bag 124. Once under the sealing head assembly 78, the storage bag 124 opening is between the two electrodes 84, 86 and the air cylinder 81 is extended and the RF electrodes 84, 86 are turned on to seal the storage bag 124 with the device case 74 and cell-filled device in a storage medium inside.

Once the cell-filled device case 74 is safely in the storage bag 124, the storage bag 124 is ready to be shipped to a surgical or implantation site. In an operation 326, a sterile shipping bag 126 is placed in the shipping bag holder 118 and the sealed device case storage bag 124 is inserted therein. To seal the shipping bag 126, the unsealed or opened portion of the bag 126 is placed under the sealing bar 122, which is lowered and the heat self-actuated to seal the shipping bag 126.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. In particular, embodiments of the invention need not include all of the features nor have all of the advantages described herein. Rather, they may possess any subset or combination of features and advantages. Accordingly, the described embodiments are to be considered in all respects as only illustrative and not restrictive.

We claim:

1. A method of loading an implantable device with cells, the method comprising:
    (a) obtaining a container comprising a flushing volume, a cell volume, and a priming volume;
    (b) aspirating first the flushing volume, then the cell volume, and then the priming volume from the container into a dosing tube assembly under negative pressure generated by a pump, wherein a first end portion of the dosing tube assembly is detachably coupled to the pump; and
    (c) dispensing first the priming volume, then the cell volume, and then the flushing volume from the dosing tube assembly into the implantable device through an implantable device port under positive pressure generated by the pump, wherein during the act of dispensing, a second end portion of the dosing tube assembly is detachably connected to the device port, such that the implantable device becomes loaded with cells.

2. The method of claim 1, wherein the first end portion of the dosing tube assembly is detachably connected to a syringe that is detachably connected to the pump.

3. The method of claim 1, wherein the dosing tube assembly comprises a fluidic reservoir and a dosing tube.

4. The method of claim 3, wherein the first end portion of the dosing tube assembly comprises the fluidic reservoir.

5. The method of claim 4, wherein the flushing volume, the cell volume, and the priming volume once aspirated are contained in the fluidic reservoir.

6. The method of claim 3, wherein the second end portion of the dosing tube assembly comprises the dosing tube.

7. The method of claim 6, wherein during the act of dispensing, the dosing tube is detachably connected to the device port by a fitting.

8. The method of claim 1, wherein the cells are pancreatic lineage cells or the cells are pancreatic lineage cell aggregates.

9. The method of claim 8, wherein the pancreatic lineage cells or pancreatic lineage cell aggregates are pancreatic progenitor cells, PDX-1 positive pancreatic progenitor cells, pancreatic endoderm cells, endocrine precursor cells, endocrine cells, immature beta cells, or immature islet cells.

10. The method of claim 1, wherein the method is automated, semi-automated, or manual.

11. The method of claim 1, further comprising (d) sealing the device port after step (c).

12. The method of claim 1, wherein the implantable device comprises multiple device ports, wherein step (b) comprises aspirating multiple sets of a flushing volume, a cell volume, and a priming volume into the dosing tube assembly from the container and wherein step (c) comprises dispensing each set of a priming volume, a cell volume, and a flushing volume into the implantable device via one of the device ports.

13. The method of claim 1, wherein the implantable device comprises multiple implantable devices, wherein step (b) comprises aspirating multiple sets of a flushing volume, a cell volume, and a priming volume into the dosing tube assembly from the container and wherein step (c) comprises dispensing each set of a priming volume, a cell volume, and a flushing volume into one of the implantable devices.

14. A method of loading an implantable device with cells, the method comprising:
(a) obtaining a container comprising a flushing volume, a cell volume, and a priming volume;
(b) aspirating first the flushing volume, then the cell volume, and then the priming volume from the container into a dosing tube assembly; and
(c) dispensing first the priming volume, then the cell volume, and then the flushing volume from the dosing tube assembly into the implantable device through an implantable device port, such that the implantable device is loaded with cells.

15. The method of claim 14, wherein the flushing volume comprises a liquid substantially without cells, the cell volume comprises the liquid with suspended cells, and the priming volume comprises the liquid substantially without the cells.

16. The method of claim 14, wherein step (b) comprises (i) aspirating the flushing volume from the container, wherein the flushing volume comprises a liquid substantially without cells, (ii) applying positive pressure with a pump to the container to resuspend cells within the container, (iii) aspirating the cell volume from the container, wherein the cell volume comprises the liquid with suspended cells, and (iii) aspirating the priming volume from the container, wherein the priming volume comprises the liquid substantially without the cells.

17. The method of claim 14, wherein step (b) comprises aspirating first the flushing volume, then the cell volume, and then the priming volume from the container into the dosing tube assembly under negative pressure generated by a pump while a first end portion of the dosing tube assembly is fluidly coupled to the pump and a tip of a second end portion of the dosing tube assembly is inserted into the container, and step (c) comprises dispensing first the priming volume, then the cell volume, and then the flushing volume from the dosing tube assembly into the implantable device through the implantable device port under positive pressure generated by the pump while the first end portion of the dosing tube assembly is fluidly coupled to the pump and the tip of the second end portion of the dosing tube assembly is connected to the implantable device port.

* * * * *